(12) United States Patent
Pirotte et al.

(10) Patent No.: US 6,242,443 B1
(45) Date of Patent: *Jun. 5, 2001

(54) 1,2,4-BENZOTHIADIAZINE DERIVATIVES, THEIR PREPARATION AND USE

(75) Inventors: Bernard Pirotte, Oupeye; Philippe Lebrun, Bruxelles; Pascal De Tullio; Fabian Somers, both of Liege; Jacques Delarge, Delembreux, all of (BE); John Bondo Hansen, Jyderup (DK); Flemming Elmelund Nielsen, Virum (DK); Holger Claus Hansen, Værløse (DK); John Patrick Mogensen, Vanløse (DK); Tina Møller-Tagmose, Farum (DK)

(73) Assignee: Novo Nordisk AIS, Bagsvaerd (DK)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/877,456

(22) Filed: Jun. 17, 1997

(30) Foreign Application Priority Data

Jun. 21, 1996 (DK) .................................................. 0693/96
Dec. 19, 1996 (DK) .................................................. 1451/96

(51) Int. Cl.$^7$ ..................... C07D 285/24; A61K 31/5415
(52) U.S. Cl. ............................................ 514/223.2; 544/12
(58) Field of Search .................................. 514/223.2, 12

(56) References Cited

U.S. PATENT DOCUMENTS 3,269,906   8/1966   Topliss et al. ..................... 544/11

FOREIGN PATENT DOCUMENTS 1 470 316   4/1969  (DE) .
7604521    7/1978  (SE) .

OTHER PUBLICATIONS

Wollweber et al., Arzneim–Forsch./Drug Res., vol. 31 (I) No. 2, pp. 279–288 (1981).
Cronin et al., Journal of Medicinal Chemistry, vol. 11, pp. 136–138 (1968).
L. Raffa et al., IL Farmaco—Ed. Sc., vol. 29, No. 6, pp. 411–423 (1974).
L. Raffa et al., Farmaco Ed. Scientifica, vol. 20, pp. 647–661 (1965).
E. Grana et al., IL Farmaco—Ed. Sc., vol. XVII, No. 12 pp. 975–987 (1962).
Pirotte et al., J. Med. Chem., vol. 36, pp. 3211–3213 (1993).
Petersen, Acta Chemica Scandinavica, vol. 27, No. 7, pp. 2655–2660.

*Primary Examiner*—John M. Ford
(74) *Attorney, Agent, or Firm*—Steve T. Zelson, Esq.; Carol E. Rozek, Esq.

(57) ABSTRACT

1,2,4-Benzothiadiazine derivatives represented by formula

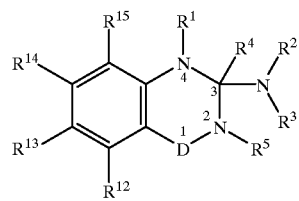

wherein D, $R^1$, $R^2$, $R^3$, $R^4$, $R^5$, $R^{12}$, $R^{13}$, $R^{14}$, $R^{15}$ are defined in the description, composition thereof and methods for preparing the compounds are described.

The compounds are useful in the treatment of diseases of the central nervous system, the cardiovascular system, the pulmonary system, the gastrointestinal system and the endocrinological system.

55 Claims, No Drawings

US 6,242,443 B1

1,2,4-BENZOTHIADIAZINE DERIVATIVES, THEIR PREPARATION AND USE

CROSS-REFERENCE TO RELATED APPLICATIONS

This application claims priority under 35 U.S.C. 119 of Danish application 0693/96 filed Jun. 21, 1996, and 1451/96 filed Dec. 19, 1996, the contents of which are fully incorporated herein by reference.

FIELD OF THE INVENTION

The present invention relates to 1,2,4-benzothiadiazine derivatives, to methods for their preparation, to compositions comprising the compounds, to the use of these compounds as medicaments and their use in therapy e.g. in the treatment of diseases of the central nervous system, the cardiovascular system, the pulmonary system, the gastrointestinal system and the endocrinological system.

BACKGROUND OF THE INVENTION

Potassium channels play an important role in membrane potential. Among the different types of potassium channels are the ATP-sensitive ($K_{ATP}$-) channels which are regulated by changes in the intracellular concentration of adenosine triphosphate. The $K_{ATP}$-channels have been found in cells from various tissues such as cardiac cells, pancreatic cells, skeletal muscles, smooth muscles, central neurons and adenohypophysis cells. The channels have been associated with diverse cellular functions for example hormone secretion (insulin from pancreatic beta-cells, growth hormone and prolactin from adenohypophysis cells), vasodilation (in smooth muscle cells), cardiac action potential duration, neurotransmitter release in the central nervous system.

Modulators of the $K_{ATP}$-channels have been found to be of importance for the treatment of various diseases. Certain sulphonylureas which have been used for the treatment of non-insulin-dependent diabetes mellitus act by stimulating insulin release through an inhibition of the $K_{ATP}$-channels on pancreatic beta-cells.

The potassium channel openers, which comprise a heterogeneous group of compounds, have been found to be able to relax vascular smooth muscles and have therefore been used for the treatment of hypertension.

In addition, potassium channel openers can be used as bronchodilators in the treatment of asthma and various other diseases.

Furthermore, potassium channel openers have been shown to promote hairgrowth, and have been used for the treatment of baldness.

Potassium channel openers are also able to relax urinary bladder smooth muscle and therefore, can be used for the treatment of urinary incontinence. Potassium channel openers which relax smooth muscle of the uterus can be used for treatment of premature labor.

By acting on potassium channels of the central nervous system these compounds can be used for treatment of various neurological and psychiatric diseases such as Alzheimer, epilepsy and cerebral ischemia.

Further, the compounds are found to be useful in the treatment of benign prostatic hyperplasia, erectile dysfunction and in contraception.

Compounds of the present invention, which inhibit insulin secretion by activating potassium channels of the beta-cell can be used in combination with compounds which reduce blood glucose levels. Examples of such compounds are insulin, insulin sensitizers, such as thiazolidinediones, insulin secretagogues, such as repaglinide, tolbutamide, glibenclamide and glucagon like peptide (GLP1), inhibitors of α-glucosidases and hepatic enzymes responsible for the biosynthesis of glucose, and glucagon.

Recently, it has been shown that Diazoxide (7-chloro-3-methyl-2H-1,2,4-benzothiadiazine 1,1-dioxide) and certain 3-(alkylamino)-4H-pyrido[4,3-e]-1,2,4-thiadiazine 1,1-dioxide derivatives inhibit insulin release by an activation of $K_{ATP}$-channels on pancreatic beta-cells (Pirotte B. et al. *Biochem. Pharmacol*, 47, 1381–1386 (1994); Pirotte B. et al., *J. Med. Chem.*, 36, 3211–3213 (1993). Diazoxide has furthermore been shown to delay the onset of diabetes in BB-rats (Vlahos W D et al. *Metabolism* 40, 39–46 (1991). In obese zucker rats diazoxide has been shown to decrease insulin secretion and increase insulin receptor binding and consequently improve glucose tolerance and decrease weight gain (Alemzadeh R. et al. Endocrinol. 133, 705–712, 1993). It is expected that compounds which activate $K_{ATP}$-channels can be used for treatment of diseases characterised by an overproduction of insulin and for the treatment and prevention of diabetes.

The following compounds are known from the literature:
3-isopropylamino-4H-1,2,4-benzothiadiazine 1,1-dioxide
3-isobutylamino-4H-1,2,4-benzothiadiazine 1,1-dioxide
(2-ethylhexylamino)-4H-1,2,4-benzothiadiazine 1,1-dioxide
cyclopropylamino-4H-1,2,4-benzothiadiazine 1,1-dioxide
cyclohexylamino-4H-1,2,4-benzothiadiazine 1,1-dioxide
7-chloro-3-(1,2,2-trimethylpropylamino)-4H-1,2,4-benzothiadiazine 1,1-dioxide
7-chloro-3-(1,2-dimethylpropylamino)-4H-1,2,4-benzothiadiazine 1,1-dioxide
7-chloro-3-(1-methylpropylamino)-4H-1,2,4-benzothiadiazine 1,1-dioxide
7-chloro-3-isopropylamino-4H-1,2,4-benzothiadiazine 1,1-dioxide
7-chloro-3-cyclopropylamino-4H-1,2,4-benzothiadiazine 1,1-dioxide
7-chloro-3-cyclohexylamino-4H-1,2,4-benzothiadiazine 1,1-dioxide
6-chloro-3-isopropylamino-4H-1,2,4-benzothiadiazine 1,1-dioxide
6-chloro-3-cyclopropylamino-4H-1,2,4-benzothiadiazine 1,1-dioxide
6,7-dichloro-3-isopropylamino-4H-1,2,4-benzothiadiazine 1,1-dioxide
6,7-dichloro-3-cyclopropylamino-4H-1,2,4-benzothiadiazine 1,1-dioxide
3-isobutylamino-7-methyl-4H-1,2,4-benzothiadiazine 1,1-dioxide
3-cyclopentylamino-7-methyl-4H-1,2,4-benzothiadiazine 1,1-dioxide
3-cyclohexylamino-6-trifluoromethyl-4H-1,2,4-benzothiadiazine 1,1-dioxide
(N-cyclohexyl-N-methylamino)-4H-1,2,4-benzothiadiazine 1,1-dioxide
3-cyclohexylamino-4-methyl-4H-1,2,4-benzothiadiazine 1,1-dioxide
3-cyclohexylamino-2-methyl-2H-1,2,4-benzothiadiazine 1,1-dioxide.

DESCRIPTION OF THE INVENTION

The present invention relates to 1,2,4-benzothiadiazine derivatives of the general formula I:

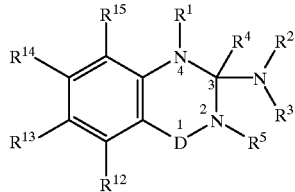

wherein $R^1$ and $R^5$ independently can be hydrogen; hydroxy; $C_{1-6}$-alkoxy; $C_{3-6}$-cycloalkyl optionally mono- or polysubstituted with $C_{1-6}$-alkyl, halogen, hydroxy or $C_{1-6}$-alkoxy; or $C_{1-6}$-alkyl, $C_{2-6}$-alkenyl or $C_{2-4}$-alkynyl optionally mono- or polysubstituted with halogen and $R^4$ is hydrogen; or $R^4$ together with $R^5$ represent one of the bonds in a double bond between the atoms 2 and 3 of formula I and $R^1$ is as defined above; or $R^4$ together with $R^1$ represent one of the bonds in a double bond between the atoms 3 and 4 of formula I and $R^5$ is as defined above;

D represents —S(=O)$_2$— or —S(=O)—;

$R^2$ is hydrogen; hydroxy; $C_{1-6}$-alkoxy; $C_{3-6}$-cycloalkyl optionally mono- or polysubstituted with $C_{1-6}$-alkyl, halogen, hydroxy or $C_{1-6}$-alkoxy; or $C_{1-6}$-alkyl, $C_{2-6}$-alkenyl or $C_{2-6}$-alkynyl optionally mono- or polysubstituted with halogen;

$R^3$ is $R^8$; —OR$^8$; —C(=X$^1$)R$^8$; bicycloalkyl, aryl, heteroaryl, arylalkyl or heteroarylalkyl optionally mono- or polysubstituted with halogen, hydroxy, $C_{1-6}$-alkyl, $C_{1-6}$-alkoxy, aryloxy, arylalkoxy, nitro, amino, $C_{1-6}$-monoalkyl- or dialkylamino, cyano, oxo, acyl or $C_{1-6}$-alkoxycarbonyl;

wherein $R^8$ is hydrogen; $C_{3-6}$-cycloalkyl or ($C_{3-6}$-cycloalkyl)$C_{1-6}$-alkyl the $C_{3-6}$-cycloalkyl group optionally being mono- or polysubstituted with $C_{1-6}$-alkyl, halogen, hydroxy or $C_{1-6}$-alkoxy; a 3–6 membered saturated ring system comprising one or more nitrogen-, oxygen- or sulfur atoms, optionally being mono- or polysubstituted with halogen, cyano, trifluoromethyl, $C_{1-6}$-alkyl, $C_{1-6}$-alkoxy, $C_{1-6}$-alkoxy-$C_{1-6}$-alkyl, aryl, arylalkyl, hydroxy, oxo, nitro, amino, $C_{1-6}$-monoalkyl or dialkylamino; or straight or branched $C_{1-8}$-alkyl optionally mono- or polysubstituted with halogen, hydroxy, $C_{1-6}$-alkoxy, $C_{1-6}$-alkylthio, $C_{3-6}$-cycloalkyl, aryl, aryloxy, arylalkoxy, nitro, amino, $C_{1-6}$-monoalkyl- or dialkylamino, cyano, oxo, formyl, acyl, carboxy, $C_{1-6}$-alkoxycarbonyl, carbamoyl, formylamino, or $C_{1-6}$-alkylcarbonylamino;

$X^1$ is O or S;
$R^3$ is

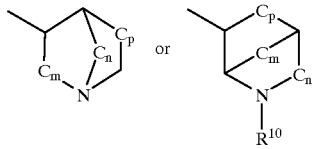

wherein n,m,p independently can be 0,1,2,3 and $R^{10}$ is hydrogen; hydroxy; $C_{1-6}$-alkoxy; $C_{3-6}$-cycloalkyl optionally mono- or polysubstituted with $C_{1-6}$-alkyl, halogen, hydroxy or $C_{1-6}$-alkoxy; or $C_{1-6}$-alkenyl or $C_{2-6}$-alkynyl optionally mono- or polysubstituted with halogen;

$R^{12}$, $R^{13}$, $R^{14}$, $R^{15}$ independently are hydrogen; halogen; $C_{1-18}$-alkyl; $C_{3-6}$-cycloalkyl; hydroxy; $C_{1-6}$-alkoxy; $C_{1-6}$-alkoxy-$C_{1-6}$-alkyl; nitro; amino; cyano; cyanomethyl; perhalomethyl; $C_{1-6}$-monoalkyl- or dialkylamino; sulfamoyl; $C_{1-6}$-alkylthio; $C_{1-6}$-alkylsulfonyl; $C_{1-6}$-alkylsulfinyl; $C_{1-6}$-alkylcarbonylamino; formyl; arylthio, arylsulfinyl, arylsulfonyl, the aryl group optionally being mono- or polysubstituted with $C_{1-6}$-alkyl, halogen, hydroxy or $C_{1-6}$-alkoxy; $C_{1-6}$-alkoxycarbonyl; $C_{1-6}$-alkoxycarbonyl-$C_{1-6}$-alkyl; carbamyl; carbamylmethyl; $C_{1-6}$-monoalkyl- or dialkylaminocarbonyl; $C_{1-6}$-monoalkyl- or dialkylaminothiocarbonyl; ureido; $C_{1-6}$-monoalkyl- or dialkylaminocarbonylamino, thioureido; $C_{1-6}$-monoalkyl- or dialkylaminothiocarbonylamino; $C_{1-6}$-monoalkyl- or dialkylaminosulfonyl; carboxy; carboxy-$C_{1-6}$-alkyl; acyl; aryl, arylalkyl, aryloxy, the aryl group optionally being mono- or polysubstituted with $C_{1-6}$-alkyl, halogen, hydroxy or $C_{1-6}$alkoxy; (1,2,4-oxadiazol-5-yl)- or (1,2,4-oxadiazol-3-yl)-$C_{1-6}$-alkyl the oxadiazolyl group optionally being substituted with $C_{1-6}$-alkyl or $C_{3-6}$-cycloalkyl; or a 5–6 membered nitrogen containing ring, optionally substituted with phenyl or $C_{1-6}$-alkyl;

Within its scope the invention includes all optical isomers of compounds of formula I, some of which are optically active, and also their mixtures including racemic mixture thereof.

The scope of the invention also includes all tautomeric forms of the compounds of formula I The salts include pharmaceutically acceptable acid addition salts, pharmaceutically acceptable metal salts or optionally alkylated ammonium salts, such as hydrochloric, hydrobromic, hydroiodic, phosphoric, sulfuric, trifluoroacetic, trichloroacetic, oxalic, maleic, pyruvic, malonic, succinic, citric, tartaric, fumaric, mandelic, benzoic, cinnamic, methanesulfonic, ethane sulfonic, picric and the like, and include acids related to the pharmaceutically acceptable salts listed in Journal of Pharmaceutical Science, 66, 2 (1977) and incorporated herein by reference, or lithium, sodium, potassium, magnesium and the like.

The term "$C_{1-6}$-alkyl" as used herein, alone or in combination, refers to a straight or branched, saturated hydrocarbon chain having 1 to 6 carbon atoms such as e.g. methyl, ethyl, n-propyl, isopropyl, n-butyl, sec-butyl, isobutyl, tert-butyl, n-pentyl, 2-methylbutyl, 3-methylbutyl, n-hexyl, 4-methylpentyl, neopentyl, n-hexyl, 1,2-dimethylpropyl, 2,2-dimethylpropyl and 1,2,2-trimethylpropyl.

The term "$C_{1-6}$-alkoxy" as used herein, alone or in combination, refers to a straight or branched monovalent substituent comprising a $C_{1-6}$-alkyl group linked through an ether oxygen having its free valence bond from the ether oxygen and having 1 to 6 carbon atoms e.g. methoxy, ethoxy, propoxy, isopropoxy, butoxy, pentoxy.

The term "$C_{1-6}$-alkylthio" as used herein, alone or in combination, refers to a straight or branched monovalent substituent comprising a lower alkyl group linked through a divalent sulfur atom having its free valence bond from the sulfur atom and having 1 to 6 carbon atoms e.g. methylthio, ethylthio, propylthio, butylthio, pentylthio.

The term "$C_{2-6}$-alkenyl" as used herein refers to an unsaturated hydrocarbon chain having 2–6 carbon atoms and one double bond such as e.g. vinyl, 1-propenyl, allyl, isopropenyl, n-butenyl, n-pentenyl and n-hexenyl.

The term "$C_{3-6}$-cycloalkyl" as used herein refers to a radical of a saturated cyclic hydrocarbon with the indicated number of carbons such as cyclopropyl, cyclobutyl, cyclopentyl, or cyclohexyl.

The term "$C_{1-6}$-alkynyl" as used herein refers to unsaturated hydrocarbons which contain triple bonds, such as e.g. —C≡CH, —C≡CCH$_3$, —CH$_2$C≡CH, —CH$_2$CH$_2$C≡CH, —CH(CH$_3$)C≡CH, and the like.

The term "$C_{1-6}$-alkoxy-$C_{1-6}$-alkyl" as used herein refers to a group of 2–12 carbon atoms interrupted by an O such as e.g. CH$_2$—O—CH$_3$, CH$_2$—O—CH$_2$—CH$_3$, CH$_2$—O—CH(CH$_3$)$_2$ and the like.

The term "halogen" means fluorine, chlorine, bromine or iodine.

The term "perhalomethyl" means trifluoromethyl, trichloromethyl, tribromomethyl or triiodomethyl.

The term "$C_{1-8}$-alkyl" as used herein refers to a straight or branched, saturated hydrocarbon chain having the indicated number of carbon atoms such as e.g. methyl, ethyl, n-propyl, isopropyl, n-butyl, sec-butyl, isobutyl, tert-butyl, n-pentyl, 2-methylbutyl, 3-methylbutyl, n-hexyl, 4-methylpentyl, neopentyl, n-hexyl, 1,2-dimethylpropyl, 2,2-dimethylpropyl, 1,2,2-trimethylpropyl and the like. The term "$C_{1-8}$-alkyl" as used herein also includes secondary $C_{3-6}$-alkyl and tertiary $C_{4-6}$-alkyl.

The term "$C_{1-6}$-monoalkylamino" as used herein refers to an amino group wherein one of the hydrogen atoms is substituted with a straight or branched, saturated hydrocarbon chain having the indicated number of carbon atoms such as e.g. methylamino, ethylamino, propylamino, n-butylamino, sec-butylamino, isobutylamino, tert-butylamino, n-pentylamino, 2-methylbutylamino, n-hexylamino, 4-methylpentylamino, neopentylamino, n-hexylamino, 2,2-dimethylpropylamino and the like.

The term "$C_{1-6}$-dialkylamino" as used herein refers to an amino group wherein the two hydrogen atoms independently are substituted with a straight or branched, saturated hydrocarbon chain having the indicated number of carbon atoms; such as dimethylamino, N-ethyl-N-methylamino, diethylamino, dipropylamino, N-(n-butyl)-N-methylamino, di(n-pentyl)amino, and the like.

The term "acyl" as used herein refers to a monovalent substituent comprising a $C_{1-6}$-alkyl group linked through a carbonyl group; such as e.g. acetyl, propionyl, butyryl, isobutyryl, pivaloyl, valeryl, and the like.

The term "$C_{1-6}$-alkoxycarbonyl" as used herein refers to a monovalent substituent comprising a $C_{1-6}$-alkoxy group linked through a carbonyl group; such as e.g. methoxycarbonyl, carbethoxy, propoxycarbonyl, isopropoxycarbonyl, n-butoxycarbonyl, sec-butoxycarbonyl, tert-butoxycarbonyl, 3-methylbutoxycarbonyl, n-hexoxycarbonyl and the like.

The term "3–6 membered saturated ring system" as used herein refers to a monovalent substituent comprising a monocyclic saturated system containing one or more hetero atoms selected from nitrogen, oxygen and sulfur and having 3–6 members and having its free valence from a carbon atom, e.g. 2-pyrrolidyl, 4-piperidyl, 3-morpholinyl, 1,4-dioxan-2-yl, 5-oxazolidinyl, 4-isoxazolidinyl, or 2-thiomorpholinyl.

The term "bicycloalkyl" as used herein refers to a monovalent substituent comprising a bicyclic structure made of 6–12 carbon atoms such as e.g. 2-norbornyl, 7-norbornyl, 2-bicyclo[2.2.2]octyl, and 9-bicyclo[3.3.1] nonanyl.

The term "aryl" as used herein refers to phenyl, 1-naphthyl, or 2-naphthyl.

The term "heteroaryl" as used herein, alone or in combination, refers to a monovalent substituent comprising a 5–6 membered monocyclic aromatic system or a 9–10 membered bicyclic aromatic system containing one or more heteroatoms selected from nitrogen, oxygen and sulfur, e.g. pyrrole, imidazole, pyrazole, triazole, pyridine, pyrazine, pyrimidine, pyridazine, isothiazole, isoxazole, oxazole, oxadiazole, thiadiazole, quinoline, isoquinoline, quinazoline, quinoxaline, indole, benzimidazole, benzofuran, pteridine, and purine.

The term "arylalkyl" as used herein refers to a straight or branched saturated carbon chain containing from 1 to 6 carbons substituted with an aromatic carbohydride; such as benzyl, phenethyl, 3-phenylpropyl, 1-naphtylmethyl, 2-(1-naphtyl)ethyl and the like.

The term "aryloxy" as used herein refers to phenoxy, 1-naphthyloxy or 2-naphthyloxy.

The term "arylalkoxy" as used herein refers to a $C_{1-6}$-alkoxy group substituted with an aromatic carbohydride, such as benzyloxy, phenethoxy, 3-phenylpropoxy, 1-naphthylmethoxy, 2-(1-naphtyl)ethoxy and the like.

The term "heteroarylalkyl" as used herein refers to a straight or branched saturated carbon chain containing from 1 to 6 carbons substituted with a heteroaryl group; such as (2-furyl)methyl, (3-furyl)methyl, (2-thienyl)methyl, (3-thienyl)methyl, (2-pyridyl)methyl, 1-methyl-1-(2-pyrmidyl)ethyl and the like.

The term "$C_{1-6}$-alkylsulfonyl" as used herein refers to a monovalent substituent comprising a $C_{1-6}$-alkyl group linked through a sulfonyl group such as e.g. methylsulfonyl, ethylsulfonyl, n-propylsulfonyl, isopropylsulfonyl, n-butylsulfonyl, sec-butylsulfonyl, isobutylsulfonyl, tert-butylsulfonyl, n-pentylsulfonyl, 2-methylbutylsulfonyl, 3-methylbutylsulfonyl, n-hexylsulfonyl, 4-methylpentylsulfonyl, neopentylsulfonyl, n-hexylsulfonyl and 2,2-dimethylpropylsulfonyl.

The term "$C_{1-6}$-monoalkylaminosulfonyl" as used herein refers to a monovalent substituent comprising a $C_{1-6}$-monoalkylamino group linked through a sulfonyl group such as e.g. methylaminosulfonyl, ethylaminosulfonyl, n-propylaminosulfonyl, isopropylaminosulfonyl, n-butylaminosulfonyl, sec-butylaminosulfonyl, isobutylaminosulfonyl, tert-butylaminosulfonyl, n-pentylaminosulfonyl, 2-methylbutylaminosulfonyl, 3-methylbutylaminosulfonyl, n-hexylaminosulfonyl, 4-methylpentylaminosulfonyl, neopentylaminosulfonyl, n-hexylaminosulfonyl and 2,2-dimethylpropylaminosulfonyl.

The term "$C_{1-6}$-dialkylaminosulfonyl" as used herein refers to a monovalent substituent comprising a $C_{1-6}$-dialkylamino group linked through a sulfonyl group such as dimethylaminosulfonyl, N-ethyl-N-methylaminosulfonyl, diethylaminosulfonyl, dipropylaminosulfonyl, N-(n-butyl)-N-methylaminosulfonyl, di(n-pentyl)aminosulfonyl, and the like.

The term "$C_{1-6}$-alkylsulfinyl" as used herein refers to a monovalent substituent comprising a straight or branched $C_{1-6}$-alkyl group linked through a sulfinyl group (—S(=O)—); such as e.g. methylsulfinyl, ethylsulfinyl, isopropylsulfinyl, butylsulfinyl, pentylsulfinyl, and the like.

The term "$C_{1-6}$-alkylcarbonylamino" as used herein refers to an amino group wherein one of the hydrogen atoms is substituted with an acyl group, such as e.g. acetamido, propionamido, isopropylcarbonylamino, and the like.

The term "($C_{3-6}$-cycloalkyl)$C_{1-6}$-alkyl" as used herein, alone or in combination, refers to a straight or branched, saturated hydrocarbon chain having 1 to 6 carbon atoms and being monosubstituted with a $C_{3-6}$-cycloalkyl group, the cycloalkyl group optionally being mono- or polysubstituted with $C_{1-6}$-alkyl, halogen, hydroxy or $C_{1-6}$-alkoxy; such as e.g. cyclopropylmethyl, (1-methylcyclopropyl)methyl, 1-(cyclopropyl)ethyl, cyclopentylmethyl, cyclohexylmethyl, and the like.

The term "arylthio" as used herein, alone or in combination, refers to an aryl group linked through a divalent sulfur atom having its free valence bond from the sulfur atom, the aryl group optionally being mono- or polysubstituted with $C_{1-6}$-alkyl, halogen, hydroxy or $C_{1-6}$-alkoxy; e.g. phenylthio, (4-methylphenyl)-thio, (2-chlorophenyl)thio, and the like.

The term "arylsulfinyl" as used herein refers to an aryl group linked through a sulfinyl group (—S(=O)—), the aryl group optionally being mono- or polysubstituted with $C_{1-6}$-alkyl, halogen, hydroxy or $C_{1-6}$-alkoxy; such as e.g. phenylsulfinyl, (4-chlorophenyl)sulfinyl, and the like.

The term "arylsulfonyl" as used herein refers to an aryl group linked through a sulfonyl group, the aryl group optionally being mono- or polysubstituted with $C_{1-6}$-alkyl, halogen, hydroxy or $C_{1-6}$-alkoxy; such as e.g. phenylsulfonyl, tosyl, and the like.

The term "$C_{1-6}$-monoalkylaminocarbonyl" as used herein refers to a monovalent substituent comprising a $C_{1-6}$-monoalkylamino group linked through a carbonyl group such as e.g. methylaminocarbonyl, ethylaminocarbonyl, n-propylaminocarbonyl, isopropylaminocarbonyl, n-butylaminocarbonyl, sec-butylaminocarbonyl, isobutylaminocarbonyl, tert-butylaminocarbonyl, n-pentylaminocarbonyl, 2-methylbutylaminocarbonyl, 3-methylbutylamino-carbonyl, n-hexylaminocarbonyl, 4-methylpentylaminocarbonyl, neopentylaminocarbonyl, n-hexylaminocarbonyl and 2-2-dimethylpropylaminocarbonyl.

The term "$C_{1-6}$-dialkylaminocarbonyl" as used herein refers to a monovalent substituent comprising a $C_{1-6}$-dialkylamino group linked through a carbonyl group such as dimethylaminocarbonyl, N-ethyl-N-methylaminocarbonyl, diethylaminocarbonyl, dipropylaminocarbonyl, N-(n-butyl)-N-methylaminocarbonyl, di(n-pentyl)aminocarbonyl, and the like.

The term "$C_{1-6}$-monoalkylaminocarbonylamino" as used herein refers to an amino group wherein one of the hydrogen atoms is substituted with a $C_{1-6}$-monoalkylaminocarbonyl group, e.g. methylaminocarbonylamino, ethylaminocarbonylamino, n-propylaminocarbonylamino, isopropylaminocarbonylamino, n-butylaminocarbonylamino, sec-butylaminocarbonylamino, isobutylaminocarbonylamino, tert-butylaminocarbonylamino, and 2-methylbutylaminocarbonylamino.

The term "$C_{1-6}$-dialkylaminocarbonylamino" as used herein refers to an amino group wherein one of the hydrogen atoms is substituted with a $C_{1-6}$-dialkylaminocarbonyl group, such as dimethylaminocarbonylamino, N-ethyl-N-methylaminocarbonylamino, diethylaminocarbonylamino, dipropylaminocarbonylamino, N-(n-butyl)-N-methylaminocarbonylamino, di(n-pentyl)aminocarbonylamino, and the like.

The term "5- or 6-membered nitrogen containing ring" as used herein refers to a monovalent substituent comprising a monocyclic unsaturated or saturated system containing one or more nitrogen atoms and having 5 or 6 members, e.g. pyrrolidinyl, pyrrolinyl, imidazolidinyl, pyrazolidinyl, pyrazolinyl, piperidyl, piperazinyl, pyrrolyl, 2H-pyrrolyl, imidazolyl, pyrazolyl, triazolyl, pyridyl, pyrazinyl, pyrimidinyl, pyridazinyl, morpholino, thiomorpholino, isothiazolyl, isoxazolyl, oxazolyl, oxadiazolyl, thiadiazolyl, 1,3-dioxolanyl, and 1,4-dioxolanyl.

In a preferred embodiment of the invention one of $R^1$ and $R^5$ is hydrogen; hydroxy; $C_{1-6}$-alkoxy; $C_{3-6}$-cycloalkyl optionally mono- or polysubstituted with $C_{1-6}$-alkyl, halogen, hydroxy or $C_{1-6}$-alkoxy; $C_{1-6}$-alkyl, $C_{2-6}$-alkenyl or $C_{2-6}$-alkynyl optionally mono- or polysubstituted with halogen; and the other of $R^1$ and $R^5$ together with $R^4$ is a bond. Preferably one of $R^1$ and $R^5$ is hydrogen; and the other of $R^1$ and $R^5$ together with $R^4$ is a bond.

In another preferred embodiment of the invention $R^2$ is hydrogen or $C_{1-6}$-alkyl. Preferably $R^2$ is hydrogen.

In another preferred embodiment of the invention $R^3$ is $R^8$, —$OR^8$; —$C(=O)R^8$; wherein $R^8$ is hydrogen; $C_{3-6}$-cycloalkyl or ($C_{3-6}$-cycloalkyl)$C_{1-6}$-alkyl, $C_{3-6}$-cycloalkyl optionally being mono- or polysubstituted with $C_{1-6}$-alkyl, halogen, hydroxy or $C_{1-6}$-alkoxy; a 3–6 membered saturated ring system comprising one or more nitrogen-, oxygen- or sulfur atoms; or straight or branched $C_{1-8}$-alkyl optionally mono- or polysubstituted with halogen, $C_{3-6}$-cycloalkyl, hydroxy or $C_{1-6}$-alkoxy;

In yet another preferred embodiment of the invention $R^3$ is selected from secondary $C_{3-6}$-alkyl, tertiary $C_{4-6}$-alkyl, $C_{3-6}$-cycloalkyl or ($C_{3-6}$-cycloalkyl)methyl optionally mono- or polysubstituted with $C_{1-6}$-alkyl, halogen, hydroxy or $C_{1-6}$-alkoxy. Preferably $R^3$ is selected from isopropyl, 1-methylpropyl, 2-methylpropyl, tert-butyl, 1,1-dimethylpropyl, 1,2-dimethylpropyl, 1,2,2-trimethylpropyl, 2,3-dimethylbutyl, 1-ethylpropyl, 1-ethyl-2-methylpropyl, 1-ethyl-2,2-dimethylpropyl, 2,3,3-trimethylbutyl, 2-methylbutyl, cyclopropyl, 1-methylcyclopropyl, cyclobutyl, cyclopentyl, cyclohexyl, cyclopropylmethyl, 1-(cyclopropyl)ethyl, cyclobutylmethyl, cyclopentylmethyl or cyclohexylmethyl.

In another preferred embodiment of the invention $R^{12}$, $R^{13}$, $R^{14}$, $R^{15}$ are selected from hydrogen; halogen; $C_{1-18}$-alkyl; $C_{3-6}$-cycloalkyl; cyano; cyanomethyl; perhalomethyl; sulfamoyl; $C_{1-6}$-alkylthio; $C_{1-6}$-alkylsulfonyl; $C_{1-6}$-alkylsulfinyl; arylthio, arylsulfinyl, arylsulfonyl, the aryl group optionally being mono- or polysubstituted with $C_{1-6}$-alkyl, halogen, hydroxy or $C_{1-6}$-alkoxy; $C_{1-6}$-alkoxycarbonyl-$C_{1-6}$-alkyl; carbamylmethyl; carboxy-$C_{1-6}$-alkyl; aryloxy; (1,2,4-oxadiazol-5-yl)- or (1,2,4-oxadiazol-3-yl)$C_{1-6}$-alkyl, the oxadiazolyl group optionally being substituted with $C_{1-6}$-alkyl or $C_{3-6}$-cycloalkyl; acyl; or a 5–6 membered nitrogen containing ring, optionally substituted with phenyl of $C_{1-6}$-alkyl.

Preferred compounds of the invention are:
3-Benzyloxyamino-7-chloro-4H-1,2,4-benzothiadiazine 1,1-dioxide
7-Chloro-3-methoxyamino-4H-1,2,4-benzothiadiazine 1,1-dioxide
7-Bromo-3-isopropylamino-4H-1,2,4-benzothiadiazine 1,1-dioxide
7-Chloro-3-(N-ethyl-N-methylamino)-4H-1,2,4-benzothiadiazine 1,1-dioxide 6-Chloro-3-methoxyamino-4H-1,2,4-benzothiadiazine 1,1-dioxide
6-Chloro-3-(1,2,2-trimethylpropyl)amino-4H-1,2,4-benzothiadiazine 1,1-dioxide
7-Bromo-3-(1,2,2-trimethylpropyl)amino-4H-1,2,4-benzothiadiazine 1,1-dioxide
6-Chloro-3-(N-ethyl-N-methylamino)-4H-1,2,4-benzothiadiazine 1,1-dioxide
5-Amino-7-chloro-3-isopropylamino-4H-1,2,4-benzothiadiazine 1,1-dioxide
7-Chloro-3-(1,3-dimethylpentyl)amino-4H-1,2,4-benzothiadiazine 1,1-dioxide
7-Chloro-3-(1,5-dimethylhexyl)amino-4H-1,2,4-benzothiadiazine 1,1-dioxide
7-Chloro-3-(1,4-dimethylpentyl)amino-4H-1,2,4-benzothiadiazine 1,1-dioxide
5,7-Dichloro-3-isopropylamino-4H-1,2,4-benzothiadiazine 1,1-dioxide
7-Bromo-6-trifluoromethyl-3-isopropylamino-4H-1,2,4-benzothiadiazine 1,1-dioxide
7-Chloro-3-(3,3-diphenylpropylamino)-4H-1,2,4-benzothiadiazine 1,1-dioxide
7-Chloro-3-(4-phenylbutylamino)-4H-1,2,4-benzothiadiazine 1,1-dioxide
7-Chloro-3-(3-diethylamino-1-methylpropylamino)-4H-1,2,4-benzothiadiazine 1,1-dioxide
3-Isopropylamino-4H-1,2,4-benzothiadiazine-5-carboxaldehyde 1,1-dioxide
3-Isopropylamino-4H-1,2,4-benzothiadiazine-7-carboxaldehyde 1,1-dioxide
3-Isopropylamino-4H-1,2,4-benzothiadiazine-6-carboxylic acid 1,1-dioxide
7-Cyano-3-isopropylamino-4H-1,2,4-benzothiadiazine 1,1-dioxide
6-Chloro-7-iodo-3-isopropylamino-4H-1,2,4-benzothiadiazine 1,1-dioxide
6-Chloro-3-cyanomethylamino-4H-1,2,4-benzothiadiazine 1,1-dioxide
5,7-Dichloro-3-isopropylamino-6-trifluoromethyl-4H-1,2,4-benzothiadiazine 1,1-dioxide
7-Chloro-3-(3-(1H-imidazol-4-yl)propyl)amino-4H-1,2,4-benzothiadiazine 1,1-dioxide
3-Isopropylamino-6,7-dimethoxy-4H-1,2,4-benzothiadiazine 1,1-dioxide
3-(1-Azabicyclo[2.2.2]oct-3-yl)amino-7-chloro-4H-1,2,4-benzothiadiazine 1,1-dioxide
6-Chloro-3-(1,2-dimethylpropyl)amino-4H-1,2,4-benzothiadiazine 1,1-dioxide
6-Chloro-3-(1,2-dimethylpropyl)amino-7-sulfamoyl-4H-1,2,4-benzothiadiazine 1,1-dioxide
3-Anilino-7-chloro-4H-1,2,4-benzothiadiazine 1,1-dioxide
7-Chloro-3-(imidazol-2-yl)amino-4H-1,2,4-benzothiadiazine 1,1-dioxide
7-Chloro-3-(4-pyridyl)amino-4H-1,2,4-benzothiadiazine 1,1-dioxide
6-Chloro-3-isobutylamino-4H-1,2,4-benzothiadiazine 1,1-dioxide
3-sec-Butylamino-6-chloro-4H-1,2,4-benzothiadiazine 1,1-dioxide
6-Chloro-3-cyclohexylmethylamino-4H-1,2,4-benzothiadiazine 1,1-dioxide
6-Fluoro-3-isopropylamino-4H-1,2,4-benzothiadiazine 1,1-dioxide
3-Cyclopentylamino-6-fluoro-4H-1,2,4-benzothiadiazine 1,1-dioxide
7-Chloro-3-isopropylamino-5-nitro-4H-1,2,4-benzothiadiazine 1,1-dioxide
3-tert-Butylamino-6-chloro-4H-1,2,4-benzothiadiazine 1,1-dioxide
7-Iodo-3-isopropylamino-4H-1,2,4-benzothiadiazine 1,1-dioxide
6-Chloro-7-fluoro-3-isopropylamino-4H-1,2,4-benzothiadiazine 1,1-dioxide
3-Isopropylamino-6-trifluoromethyl-4H-1,2,4-benzothiadiazine 1,1-dioxide
7-Chloro-3-cyclopropylmethylamino-4H-1,2,4-benzothiadiazine 1,1-dioxide
3-Isopropylamino-7-methyl-4H-1,2,4-benzothiadiazine 1,1-dioxide
5,7-Dibromo-3-isopropylamino-4H-1,2,4-benzothiadiazine 1,1-dioxide
6-Acetyl-3-isopropylamino-4H-1,2,4-benzothiadiazine 1,1-dioxide
3-Allylamino-6-chloro-4H-1,2,4-benzothiadiazine 1,1-dioxide
6-Chloro-3-(1-ethylpropyl)amino-4H-1,2,4-benzothiadiazine 1,1-dioxide
6-Chloro-3-butylamino-4H-1,2,4-benzothiadiazine 1,1-dioxide
6-Chloro-3-hexylamino-4H-1,2,4-benzothiadiazine 1,1-dioxide
6,7-Dichloro-3-(1,2-dimethylpropyl)amino-4H-1,2,4-benzothiadiazine 1,1-dioxide
6,7-Dichloro-3-(1-methylbutyl)amino-4H-1,2,4-benzothiadiazine 1,1-dioxide
7-Chloro-3-(1,2-dimethylpropyl)amino-2-methyl-2H-1,2,4-benzothiadiazine 1,1-dioxide
6,8-Dichloro-3-isopropylamino-4H-1,2,4-benzothiadiazine 1,1-dioxide
7-Chloro-3-isopropylamino-2-methyl-2H-1,2,4-benzothiadiazine 1,1-dioxide
3-Isopropylamino-6-benzenesulfonyl-4H-1,2,4-benzothiadiazine 1,1-dioxide
3-Isopropylamino-6-methanesulfonyl-4H-1,2,4-benzothiadiazine 1,1-dioxide
5-Chloro-3-isopropylamino-4H-1,2,4-benzothiadiazine 1,1-dioxide
3-Isopropylamino-6-methyl-4H-1,2,4-benzothiadiazine 1,1-dioxide
6-Chloro-3-isopropylamino-7-methyl-4H-1,2,4-benzothiadiazine 1,1-dioxide
6-Ethoxycarbonylmethyl-3-isopropylamino-4H-1,2,4-benzothiadiazine 1,1-dioxide
6-Carboxymethyl-3-isopropylamino-4H-1,2,4-benzothiadiazine 1,1-dioxide
8-Chloro-3-isopropylamino-4H-1,2,4-benzothiadiazine 1,1-dioxide
6-Isopropyl-3-isopropylamino-4H-1,2,4-benzothiadiazine 1,1-dioxide
7-tert-Butyl-3-isopropylamino-4H-1,2,4-benzothiadiazine 1,1-dioxide
3-Isopropylamino-6-phenoxy-4H-1,2,4-benzothiadiazine 1,1-dioxide 6-Hexyl-3-isopropylamino-4H-1,2,4-benzothiadiazine 1,1-dioxide 6-Cyclohexyl-3-isopropylamino-4H-1,2,4-benzothiadiazine 1,1-dioxide 2-(3-Isopropylamino-1,1-dioxo-1,4-dihydro-1$\lambda^6$,2,4-benzothiadiazin-6-yl)-acetamide 6-(3-Cyclopropyl-1,2,4-oxadiazol-5-yl)methyl-3-isopropylamino-4H-1,2,4-benzothiadiazine 1,1-dioxide 6-Cyanomethyl-3-isopropylamino-4H-1,2,4-benzothiadiazine 1,1-dioxide 7-Chloro-3-(2-phenylethyl)amino-4H-1,2,4-benzothiadiazine 1,1-dioxide 3-sec-Butylamino-7-iodo-4H-1,2,4-benzothiadiazine 1,1-dioxide 7-Iodo-3-(1,2-dimethylpropyl)amino-4H-1,2,4-benzothiadiazine 1,1-dioxide 7-Iodo-3-(1,2,2-trimethylpropyl)amino-4H-1,2,4-benzothiadiazine 1,1-dioxide 7-Chloro-3-cyclohexylmethylamino-4H-1,2,4-benzothiadiazine 1,1-dioxide (R)-7-Chloro-3-(1-cyclohexylethyl)amino-4H-1,2,4-benzothiadiazine 1,1-dioxide (S)-7-Chloro-3-(1-cyclohexylethyl)amino-4H-1,2,4-benzothiadiazine 1,1-dioxide (R)-7-Chloro-3-(1-phenylethyl)amino-4H-1,2,4-benzothiadiazine 1,1-dioxide (S)-7-Chloro-3-(1-phenylethyl)amino-4H-1,2,4-benzothiadiazine 1,1-dioxide 3-Cyclohexyimethylamino-7-iodo-4H-1,2,4-benzothiadiazine 1,1-dioxide (R)-3-(1-Cyclohexylethyl)amino-7-iodo-4H-1,2,4-benzothiadiazine 1,1-dioxide (S)-3-(1-Cyclohexylethyl)amino-7-iodo-4H-1,2,4-benzothiadiazine 1,1-dioxide 3-Benzyiamino-7-iodo-4H-1,2,4-benzothiadiazine 1,1-dioxide (R)-7-Iodo-3-(1-phenylethyl)amino-4H-1,2,4-benzothiadiazine 1,1-dioxide (S)-7-Iodo-3-(1-phenylethyl)amino-4H-1,2,4-benzothiadiazine 1,1-dioxide 3-sec-Butylamino-7-bromo-4H-1,2,4-benzothiadiazine 1,1-dioxide 7-Bromo-3-(1,2-dimethylpropyl)amino-4H-1,2,4-benzothiadiazine 1,1-dioxide 7-Fluoro-3-isopropylamino-4H-1,2,4-benzothiadiazine 1,1-dioxide 3-sec-Butylamino-7-fluoro-4H-1,2,4-benzothiadiazine 1,1-dioxide 7-Fluoro-3-(1,2-dimethylpropyl)amino-4H-1,2,4-benzothiadiazine 1,1-dioxide 7-Bromo-3-cyclopropylamino-4H-1,2,4-benzothiadiazine 1,1-dioxide 7-Chloro-3-cyclobutylamino-4H-1,2,4-benzothiadiazine 1,1-dioxide 7-Chloro-3-(2,2,2-trifluoroethyl)amino-4H-1,2,4-benzothiadiazine 1,1-dioxide 3-Isopropylamino-7-nitro-4H-1,2,4-benzothiadiazine 1,1-dioxide 3-Allylamino-7-chloro-4H-1,2,4-benzothiadiazine 1,1-dioxide 7-Chloro-3-(2-methoxy-1-methylethyl)amino-4H-1,2,4-benzothiadiazine 1,1-dioxide 7-Chloro-3-(1-ethylpropyl)amino-4H-1,2,4-benzothiadiazine 1,1-dioxide 3-(1-Ethylpropyl)amino-7-iodo-4H-1,2,4-benzothiadiazine 1,1-dioxide 3-sec-Butylamino-7-nitro-4H-1,2,4-benzothiadiazine 1,1-dioxide 3-(1,2-Dimethylpropyl)amino-7-nitro-4H-1,2,4-benzothiadiazine 1,1-dioxide 7-Chloro-3-(2-hydroxypropyl)amino-4H-1,2,4-benzothiadiazine 1,1-dioxide 7-Chloro-3-(2-hydroxy-1-methylethyl)amino-4H-1,2,4-benzothiadiazine 1,1-dioxide 3-(2-Aminoethyl)amino-7-chloro-4H-1,2,4-benzothiadiazine 1,1-dioxide 7-Chloro-3-(2,2-diethoxyethyl)amino-4H-1,2,4-benzothiadiazine 1,1-dioxide 3-Ethylamino-7-fluoro-4H-1,2,4-benzothiadiazine 1,1-dioxide 7-Fluoro-3-propylamino-4H-1,2,4-benzothiadiazine 1,1-dioxide 3-Cyclopropylamino-7-fluoro-4H-1,2,4-benzothiadiazine 1,1-dioxide 3-Cyclobutylamino-7-fluoro-4H-1,2,4-benzothiadiazine 1,1-dioxide 3-Cyclopentylamino-7-fluoro-4H-1,2,4-benzothiadiazine 1,1-dioxide 3-Cyclopropylmethylamino-7-fluoro-4H-1,2,4-benzothiadiazine 1,1-dioxide 3-Allylamino-7-fluoro-4H-1,2,4-benzothiadiazine 1,1-dioxide 7-Fluoro-3-(2-methoxy-1-methylethyl)amino-4H-1,2,4-benzothiadiazine 1,1-dioxide 6-Chloro-3-cyclobutylamino-4H-1,2,4-benzothiadiazine 1,1-dioxide 6-Chloro-3-(2,2,2-trifluoroethyl)amino-4H-1,2,4-benzothiadiazine 1,1-dioxide 7-Bromo-3-methylamino-4H-1,2,4-benzothiadiazine 1,1-dioxide 7-Bromo-3-ethylamino-4H-1,2,4-benzothiadiazine 1,1-dioxide 7-Bromo-3-cyclobutylamino-4H-1,2,4-benzothiadiazine 1,1-dioxide 7-Bromo-3-(2,2,2-trifluoroethyl)amino-4H-1,2,4-benzothiadiazine 1,1-dioxide 7-Fluoro-3-methylamino-4H-1,2,4-benzothiadiazine 1,1-dioxide 7-Chloro-3-hexylamino-4H-1,2,4-benzothiadiazine 1,1-dioxide 6,7-Dichloro-3-hexylamino-4H-1,2,4-benzothiadiazine 1,1-dioxide 3-(2,2-Diethoxyethyl)amino-7-fluoro-4H-1,2,4-benzothiadiazine 1,1-dioxide 7-Fluoro-3-(2,2,2-trifluoroethyl)amino-4H-1,2,4-benzothiadiazine 1,1-dioxide 7-Bromo-3-propylamino-4H-1,2,4-benzothiadiazine 1,1-dioxide 6-Chloro-3-cyclopropylmethylamino-4H-1,2,4-benzothiadiazine 1,1-dioxide 3-Cyclopropylmethylamino-7-nitro-4H-1,2,4-benzothiadiazine 1,1-dioxide 7-Nitro-3-propylamino-4H-1,2,4-benzothiadiazine 1,1-dioxide 3-Cyclobutylamino-7-nitro-4H-1,2,4-benzothiadiazine 1,1-dioxide 6,7-Dichloro-3-cyclobutylamino-4H-1,2,4-benzothiadiazine 1,1-dioxide 7-Amino-3-isopropylamino-4H-1,2,4-benzothiadiazine 1,1-dioxide 7-Acetamido-3-isopropylamino-4H-1,2,4-benzothiadiazine 1,1-dioxide 3-Cyclobutylamino-7-methyl-4H-1,2,4-benzothiadiazine 1,1-dioxide 3-Isopropylamino-7-methoxy-4H-1,2,4-benzothiadiazine 1,1-dioxide 7-Methoxy-3-propylamino-4H-1,2,4-benzothiadiazine 1,1-dioxide 7-Chloro-3-(2-formylaminoethyl)amino-4H-1,2,4-benzothiadiazine 1,1-dioxide 3-(2-Acetylaminoethyl)amino-7-chloro-4H-1,2,4-benzothiadiazine 1,1-dioxide 5-Chloro-3-cyclobutylamino-4H-1,2,4-benzothiadiazine 1,1-dioxide 5-Chloro-3-propylamino-4H-1,2,4-benzothiadiazine 1,1-dioxide 5-Chloro-3-hexylamino-4H-1,2,4-benzothiadiazine 1,1-dioxide 6-Chloro-3-octylamino-4H-1,2,4-benzothiadiazine 1,1-dioxide 6-Chloro-3-(1,5-dimethylhexyl)amino-4H-1,2,4-benzothiadiazine 1,1-dioxide 3-Isopropylamino-7-trifluoromethyl-4H-1,2,4-benzothiadiazine 1,1-dioxide 3-sec-Butylamino-7-trifluoromethyl-4H-1,2,4-benzothiadiazine 1,1-dioxide 3-Isopropylamino-4H-1,2,4-benzothiadiazine-7-carboxylic acid 1,1-dioxide 3-sec-Butylamino-4H-1,2,4-benzothiadiazine-7-carboxylic acid 1,1-dioxide 3-Propylamino-7-trifluoromethyl-4H-1,2,4-benzothiadiazine 1,1-dioxide 3-Cyclopropylmethylamino-7-trifluoromethyl-4H-1,2,4-benzothiadiazine 1,1-dioxide 3-Propylamino-4H-1,2,4-benzothiadiazine-7-carboxylic acid 1,1-dioxide 7-Chloro-3-(pyridin-2-yl)amino-4H-1,2,4-benzothiadiazine 1,1-dioxide 3-Ethylamino-6,7-difluoro-4H-1,2,4-benzothiadiazine 1,1-dioxide 7-Fluoro-3,6-di(isopropylamino)-4H-1,2,4-benzothiadiazine 1,1-dioxide 6,8-Difluoro-3-isopropylamino-4H-1,2,4-benzothiadiazine 1,1-dioxide 6,7-Difluoro-3-isopropylamino-4H-1,2,4-benzothiadiazine 1,1-dioxide 6,7,8-Trifluoro-3-isopropylamino-4H-1,2,4-benzothiadiazine 1,1-dioxide 7-Fluoro-3-isopropylamino-6-methyl-4H-1,2,4-benzothiadiazine 1,1-dioxide 7-Chloro-3-isopropylamino-6-methoxy-4H-1,2,4-benzothiadiazine 1,1-dioxide 6,8-Dichloro-3-ethylamino-4H-1,2,4-benzothiadiazine 1,1-dioxide 6,8-Dichloro-3-propylamino-4H-1,2,4-benzothiadiazine 1,1-dioxide 6,8-Dichloro-3-cyclopropylamino-4H-1,2,4-benzothiadiazine 1,1-dioxide 6,8-Dichloro-3-cyclopropylmethylamino-4H-1,2,4-benzothiadiazine 1,1-dioxide 6,8-Dichloro-3-cyclobutylamino-4H-1,2,4-benzothiadiazine 1,1-dioxide 6,8-Dichloro-3-cyclopentylamino-4H-1,2,4-benzothiadiazine 1,1-dioxide 7-Chloro-3-(2-pyridyl)methylamino-4H-1,2,4-benzothiadiazine 1,1-dioxide 7-Chloro-3-(3-pyridyl)methylamino-4H-1,2,4-benzothiadiazine 1,1-dioxide 7-Chloro-3-(4-pyridyl)methylamino-4H-1,2,4-benzothiadiazine 1,1-dioxide 7-Chloro-3-(2-pyridyl)ethylamino-4H-1,2,4-benzothiadiazine 1,1-dioxide 7-Chloro-3-(3-pyridyl)ethylamino-4H-1,2,4-benzothiadiazine 1,1-dioxide 7-Chloro-3-(4-pyridyl)ethylamino-4H-1,2,4-benzothiadiazine 1,1-dioxide 6-Chloro-3-(2-pyridyl)methylamino-4H-1,2,4-benzothiadiazine 1,1-dioxide 6-Chloro-3-(3-pyridyl)methylamino-4H-1,2,4-benzothiadiazine 1,1-dioxide 6-Chloro-3-(4-pyridyl)methylamino-4H-1,2,4-benzothiadiazine 1,1-dioxide 6-Chloro-3-(2-pyridyl)ethylamino-4H-1,2,4-benzothiadiazine 1,1-dioxide 6-Chloro-3-(3-pyridyl)ethylamino-4H-1,2,4-benzothiadiazine 1,1-dioxide 6-Chloro-3-(4-pyridyl)ethylamino-4H-1,2,4-benzothiadiazine 1,1-dioxide 7-Fluoro-3-(2-pyridyl)methylamino-4H-1,2,4-benzothiadiazine 1,1-dioxide 7-Fluoro-3-(3-pyridyl)methylamino-4H-1,2,4-benzothiadiazine 1,1-dioxide 7-Fluoro-3-(4-pyridyl)methylamino-4H-1,2,4-benzothiadiazine 1,1-dioxide 7-Fluoro-3-(2-pyridyl)ethylamino-4H-1,2,4-benzothiadiazine 1,1-dioxide 7-Fluoro-3-(3-pyridyl)ethylamino-4H-1,2,4-benzothiadiazine 1,1-dioxide 7-Fluoro-3-(4-pyridyl)ethylamino-4H-1,2,4-benzothiadiazine 1,1-dioxide 6-Fluoro-3-(2-pyridyl)methylamino-4H-1,2,4-benzothiadiazine 1,1-dioxide 6-Fluoro-3-(3-pyridyl)methylamino-4H-1,2,4-benzothiadiazine 1,1-dioxide 6-Fluoro-3-(4-pyridyl)methylamino-4H-1,2,4-benzothiadiazine 1,1-dioxide 6-Fluoro-3-(2-pyridyl)ethylamino-4H-1,2,4-benzothiadiazine 1,1-dioxide 6-Fluoro-3-(3-pyridyl)ethylamino-4H-1,2,4-benzothiadiazine 1,1-dioxide 6-Fluoro-3-(4-pyridyl)ethylamino-4H-1,2,4-benzothiadiazine 1,1-dioxide 6,7-Dichloro-3-(2-pyridyl)methylamino-4H-1,2,4-benzothiadiazine 1,1-dioxide 6,7-Dichloro-3-(3-pyridyl)methylamino-4H-1,2,4-benzothiadiazine 1,1-dioxide 6,7-Dichloro-3-(4-pyridyl)methylamino-4H-1,2,4-benzothiadiazine 1,1-dioxide 6,7-Dichloro-3-(2-pyridyl)ethylamino-4H-1,2,4-benzothiadiazine 1,1-dioxide
6,7-Dichloro-3-(3-pyridyl)ethylamino-4H-1,2,4-benzothiadiazine 1,1-dioxide
6,7-Dichloro-3-(4-pyridyl)ethylamino-4H-1,2,4-benzothiadiazine 1,1-dioxide
6,8-Dichloro-3-(2-pyridyl)methylamino-4H-1,2,4-benzothiadiazine 1,1-dioxide
6,8-Dichloro-3-(3-pyridyl)methylamino-4H-1,2,4-benzothiadiazine 1,1-dioxide
6,8-Dichloro-3-(4-pyridyl)methylamino-4H-1,2,4-benzothiadiazine 1,1-dioxide
6,8-Dichloro-3-(2-pyridyl)ethylamino-4H-1,2,4-benzothiadiazine 1,1-dioxide
6,8-Dichloro-3-(3-pyridyl)ethylamino-4H-1,2,4-benzothiadiazine 1,1-dioxide
6,8-Dichloro-3-(4-pyridyl)ethylamino-4H-1,2,4-benzothiadiazine 1,1-dioxide
6,7-Difluoro-3-(2-pyridyl)methylamino-4H-1,2,4-benzothiadiazine 1,1-dioxide
6,7-Difluoro-3-(3-pyridyl)methylamino-4H-1,2,4-benzothiadiazine 1,1-dioxide
6,7-Difluoro-3-(4-pyridyl)methylamino-4H-1,2,4-benzothiadiazine 1,1-dioxide
6,7-Difluoro-3-(2-pyridyl)ethylamino-4H-1,2,4-benzothiadiazine 1,1-dioxide
6,7-Difluoro-3-(3-pyridyl)ethylamino-4H-1,2,4-benzothiadiazine 1,1-dioxide
6,7-Difluoro-3-(4-pyridyl)ethylamino-4H-1,2,4-benzothiadiazine 1,1-dioxide
6,8-Difluoro-3-(2-pyridyl)methylamino-4H-1,2,4-benzothiadiazine 1,1-dioxide
6,8-Difluoro-3-(3-pyridyl)methylamino-4H-1,2,4-benzothiadiazine 1,1-dioxide
6,8-Difluoro-3-(4-pyridyl)methylamino-4H-1,2,4-benzothiadiazine 1,1-dioxide
6,8-Difluoro-3-(2-pyridyl)ethylamino-4H-1,2,4-benzothiadiazine 1,1-dioxide
6,8-Difluoro-3-(3-pyridyl)ethylamino-4H-1,2,4-benzothiadiazine 1,1-dioxide
6,8-Difluoro-3-(4-pyridyl)ethylamino-4H-1,2,4-benzothiadiazine 1,1-dioxide
6,8-Bis(trifluoromethyl)-3-(1,4-dimethylpentyl)amino-4H-1,2,4-benzothiadiazine 1,1-dioxide
6,8-Bis(trifluoromethyl)-3-isopropylamino-4H-1,2,4-benzothiadiazine 1,1-dioxide
6,8-Bis(trifluoromethyl)-3-cyclopentylamino-4H-1,2,4-benzothiadiazine 1,1-dioxide
6,8-Bis(trifluoromethyl)-3-cyclopropylamino-4H-1,2,4-benzothiadiazine 1,1-dioxide
6,8-Bis(trifluoromethyl)-3-propylamino-4H-1,2,4-benzothiadiazine 1,1-dioxide
6,8-Bis(trifluoromethyl)-3-cyclobutylamino-4H-1,2,4-benzothiadiazine 1,1-dioxide
6.8-Bis(trifluoromethyl)-3-ethylamino-4H-1,2,4-benzothiadiazine 1,1-dioxide The compounds of the present invention interact with the potassium channels and hence act as openers or blockers of the ATP-regulated potassium channels, which make them useful in the treatment of various diseases of the cardiovascular system, e.g. cerebral ischemia, hypertension, ischemic heart diseases, angina pectoris and coronary heart diseases; the pulmonary system; the gastrointestinal system; the central nervous system and the endocrinological system.

Since some $K_{ATP}$-openers are able to antagonize vasospasms in basilar or cerebral arteries the compounds of the present invention can be used for the treatment of vasospastic disorders such as vasospastic disorders, subarachnoid haemorrhage and migraine.

The compounds of the present invention may also be used for the treatment of diseases associated with decreased skeletal muscle blood flow such as Raynauds disease and intermittent claudication.

Further, the compounds of the invention may be used for the treatment of chronic airway diseases, including asthma, and for treatment of detrusor muscle instability secondary to bladder outflow obstruction and therefore for kidney stones by aiding their passage along the urethra.

The present compounds could also be used for treatment of conditions associated with disturbances in gastrointestinal mobility such as irritable bowel syndrome. Additionally these compounds can be used for the treatment of premature labour and dysmenorrhea.

Potassium channel openers hyperpolarizes neurons and inhibit neurotransmitter release and it is expected that such compounds can be used for the treatment of various diseases of the central nervous system, e.g. epilepsia, ischemia and neurodegenerative diseases, and for the management of pain.

Further, potassium channel openers promote hairgrowth, therefore, the compounds of the present invention can be used for the treatment of baldness.

Potassium channel openers also relax urinary bladder smooth muscle, thus, the compounds of the present invention can be used for the treatment of urinary incontinence.

In diseases such as nesidioblastosis and insulinoma in which a hypersecretion of insulin causes severe hypoglycemia the compounds of the present invention can be used to reduce insulin secretion. In obesity hyperinsulinemia and insulin resistance is very frequently encountered. This condition could lead to the development of noninsulin dependent diabetes (NIDDM). It is expected that potassium channel openers and hence the compounds of the present invention can be used for reducing the hyperinsulinemia and thereby prevent diabetes and reduce obesity. In overt NIDDM treatment of hyperinsulinemia with potassium channel openers, and hence the present compounds, can be of benefit in restoring glucose sensitivity and normal insulin secretions.

In early cases of insulin dependent diabetes (IDDM) or in prediabetic cases, potassium channel openers and hence the present compounds can be used to induce betacell rest which may prevent the progression of the autoimmune disease.

The potassium channel openers of the present invention can be administered in combination with an immunosuppressant or with an agent like nicotinamide, which will reduce autoimmune degeneration of beta-cells.

Compounds of the present invention which act as blockers of $K_{ATP}$-channels can be used for the treatment of NIDDM.

Preferably, the compounds of the present invention may be used for treatment or prevention of diseases of the endocrinological system such as hyperinsulinaemia and diabetes.

Accordingly, in another aspect the invention relates to a compound of the general formula I or a pharmaceutically acceptable acid addition salt thereof for use as a therapeutically acceptable substance, preferably for use as a therapeutically acceptable substance in the treatment of hyperinsulinaemia and treatment or prevention of diabetes.

Furthermore, the invention also relates to the use of the inventive compounds of formula I as medicaments useful for treating hyperinsulinaemia and treating or preventing diabetes.

In yet another aspect, the present invention relates to methods of preparing the above mentioned compounds. The methods comprises:

a) reacting a compound of formula II:

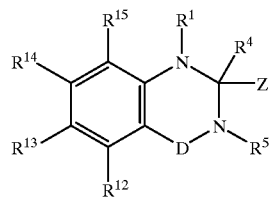

(II)

wherein D, $R^1$, $R^4$, $R^5$, $R^{12}$, $R^{13}$, $R^{14}$ and $R^{15}$ are as defined above and Z is a leaving group such as alkoxy, alkylthio, halogen, preferentially chloro, bromo, iodo, amino, trimethylamino, imidazol-1-yl, methylsulfinyl or methylsulfonyl with a compound of formula III:

(III)

wherein $R^2$ and $R^3$ are defined above to form a compound of the general formula I using e.g. procedures described by T. H. Cronon et al., *J. Med. Chem.* 11, 136 (1968); L. Raffa et al., *Farmaco Ed. Sci.* 29, 411 (1974); B. Pirotte et al., *J. Med. Chem.* 36, 3211 (1993), H. J. Petersen, Acta Chem. Scand, 27, 2655 (1973).

Another method comprises:

b) reacting a compound of formula IV:

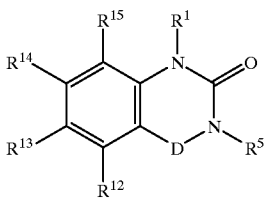

(IV)

wherein $R^1$ is hydrogen and D, $R^5$, $R^{12}$, $R^{13}$, $R^{14}$, and $R^{15}$ are as defined above, or $R^5$ is H and $R^1$, $R^{12}$, $R^{13}$, $R^{14}$, $R^{15}$ and D are as defined above, with the compound of formula III, or a suitable salt thereof in the presence of $P_2O_5$ and a high boiling tertiary amine or a suitable salt therof using a procedure described by Jensen K. G. and Pedersen E. B., *Chem. Scr.*, 20, 248–250 (1988) and Andersen L., Nielsen F. E. and Pedersen E. B., *Chem. Scr.*, 29, 45–49 (1989), to form a compound of the general formula I.

c) reacting a compound of the formula IV:

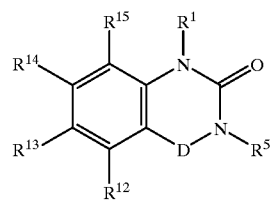

(IV)

wherein $R^1$ is hydrogen and D, $R^5$, $R^{12}$, $R^{13}$, $R^{14}$ and $R^{15}$ are as defined above or $R^5$ is H and $R^1$, $R^{12}$, $R^{13}$, $R^{14}$, $R^{15}$ and D are as defined above, with a compound of the formula III, or a suitable salt thereof in the presence of titanium tetrachloride and a solvent with which it may form a complex, like e.g. tetrahydrofuran, or a mixture of toluene and anisole, according to the methods described in R. I. Fryer, J. V. Earley, G. F. Field, W. Zally, and L. H. Sternbach, *J. Org. Chem.* 34, 1143–1145 (1969); J. B. Press et al., *J. Med. Chem.* 22, 725–731 (1979); or G. Roma et al. *Eur. J. Med. Chem.* 26, 489–496 (1991), to form a compound of the general formula I.

d) reacting a compound of formula V

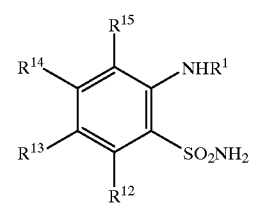

(V)

wherein $R^1$, $R^{12}$, $R^{13}$, $R^{14}$ and $R^{15}$ are as defined above, with a compound of formula VI $R^3NCO$ (VI)

wherein $R^3$ is as defined above using the method described by Chern J. W. et al., *J. Heterocycl. Chem.*, 27, 1909–1915 (1990), to form a compound of the general formula I, wherein D is $SO_2$, $R^2$ is H, and $R^4$ and $R^5$ together form a bond.

e) reacting a compound of the formula V

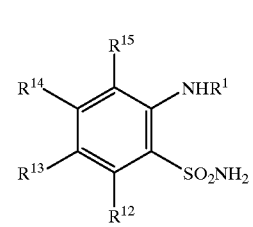

(V)

wherein $R^1$, $R^{12}$, $R^{13}$, $R^{14}$ and $R^{15}$ are as defined above, with a compound of formula VII $R^3NHC(=O)Cl$ (VII)

wherein $R^3$ is as defined above using the method described by Chern J. W. et al., *J. Heterocycl. Chem.*, 27, 1909–1915 (1990), to form a compound of the general formula I, wherein D is $SO_2$, $R^2$ is H, and $R^4$ and $R^5$ together form a bond.

f) reacting a compound of the formula V

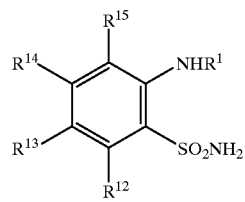

(V)

wherein $R^1, R^{12}, R^{13}, R^{14}$ and $R^{15}$ are defined as above, with a compound of formula VIII

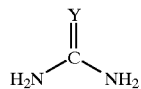

(VIII)

wherein Y is NH or S, or a suitable salt thereof using procedures described by Kotovskaya S. K. et al., *Khim.-Farm. Zh.*, 13, 54–57 (russ.) (1979) and Topliss J. G. et al., *J. Org. Chem.*, 28, 2313 (1963), to form a compound of the general formula 1, wherein D is $SO_2$, $R^4$ and $R^5$ together form a bond, and $R^2$ and $R^3$ are H.

g) reacting a compound of the formula V

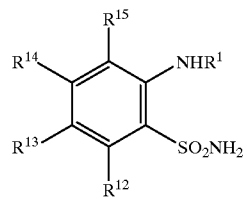

(V)

wherein $R^1, R^{12}, R^{13}, R^{14}$ and $R^{15}$ are as defined above, with a compound of formula IX

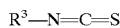

(IX)

herein $R^3$ is as defined above, using e.g. the procedures described by Topliss et al., *J. Org. Chem.*, 28, 2313 (1963), to form a compound of the general formula I, wherein D is $SO_2$, $R^2$ is H, and $R^4$ and $R^5$ together form a bond;

h) reacting in the presence of a base a compound of formula X

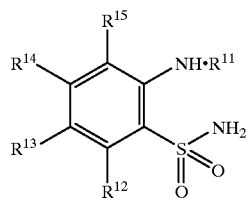

(X)

or a suitable salt thereof, wherein $R^{11}$ is $R^1$ or EtOC(=O), wherein $R^1, R^{12}, R^{13}, R^{14}$ and $R^{15}$ are as defined above, with a compound of formula IX

(IX)

wherein $R^3$ is as defined above, to form an adduct which may have either of the two structures XI or XII or be a mixture of the two (XI)

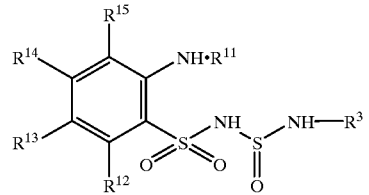

(XII)

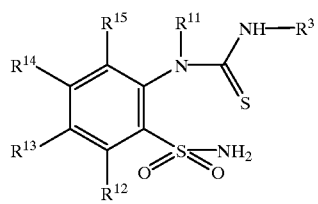

either of which by ring-closure, e.g. by treatment with phosgene in a suitable solvent, forms a compound of the general formula I, if $R^{11}$ is $R^1$, wherein D is $SO_2$, $R^2$ is H, and $R^4$ and $R^5$ together form a bond, and a compound of the general formula XIII if $R^{11}$ is EtOC(=O);

(XIII)

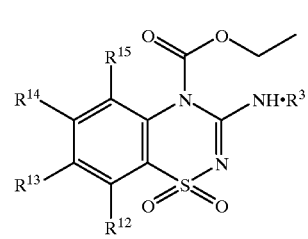

i) hydrolyzing and subsequently decarboxylating a compound of the general formula XIII (XIII)

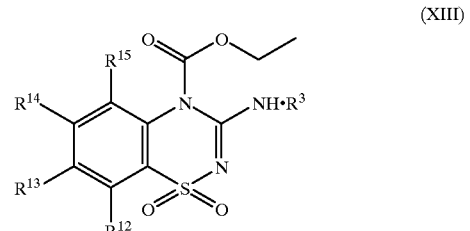

e.g. by heating the compound in aqueous base and subsequently neutralizing with an acid, to form a compound of the general formula I, wherein D is $SO_2$, $R^1$ and $R^2$ are H, and $R^4$ and $R^5$ together form a bond, and $R^3, R^{12}, R^{13}, R^{14}$ and $R^{15}$ are as defined above.

j) reacting a compound of formula

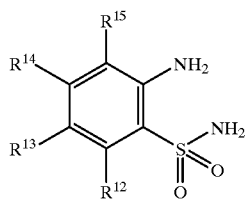

(XIV)

wherein $R^{12}$, $R^{13}$, $R^{14}$ and $R^{15}$ are as defined above with thiocarbonyldiimidazole in a suitable solvent, like e.g. dioxane, to form a compound of formula

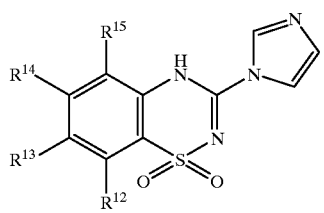

(XV)

which by treatment with an amine of formula III

(III)

forms a compound of the general formula I, wherein D is $SO_2$, $R^1$ is H, $R^4$ and $R^5$ together form a bond, and $R^2$, $R^3$, $R^{12}$, $R^{13}$, $R^{14}$ and $R^{15}$ are as defined above. The reaction may take place with or without a solvent and preferentially at elevated temperatures, e.g. in the range 100–150° C. For volatile amines, the reaction may be carried out in a sealed vessel.

Compounds of the general formula I may also undergo chemical transformations in one or more steps by conventional methods to form other compounds of the general formula I wherein D, $R^1$, $R^2$, $R^3R^4$, $R^5$, $R^{12}$, $R^{13}$, $R^{14}$ and $R^{15}$ are as defined above, e.g. by transformation of functional groups of (I) or by direct introduction of new substituents, e.g. on an aromatic ring. Such chemical transformations may consist of e.g. electrophilic substitution, nucleophilic substitution, nitration, alkylation, acylation, metalation followed by reaction with electrophiles, halogenation, reduction, oxidation, diazotization, and dehydration.

The starting materials are either known compounds or compounds which may be prepared in analogy with the preparation of known compounds or in analogy with known methods as described by e.g. Y. Girard et al., *J. Chem. Soc. Perkin I*, 1043, 1979, D. F. Hayman et al., *J. Pharm. Pharmacol.*, 522, 1962 (3-oxo-2,3-dihydro-4H-1,2,4-benzothiadiazine 1,1-dioxides), DiBella et al., *Il Farmaco Ed. Sci.* 21, 829, 1966 (3-thioxo-2,3-dihydro-4H-1,2,4-benzothiadiazine 1,1-dioxides), DiBella et al., *Il Farmaco Ed. Sci.* 27, 990, 1972 (3-methylsulfanyl-4H-1,2,4-benzothiadiazine 1,1-dioxides), Szabo, *Bull. Soc. Chim. Fr.*, 1953, 771, Bierbaum, B. A. et al., *J. Med. Chem*, 6, 1963, 272–275 (4-amino-3-sulfamoylbenzoic acid), Patent, Farbwerke Hoechst, FR 1381634, 1962 (2-chloro-5-trifluoromethyl-benzenesulfonamide and 2-benzylamino-5-trifluoromethylbenzenesulfonamide), Short, J. H.; Biermacher, U., *J. Amer. Chem. Soc.*, 82, 1960, 1135–1138 (2-amino-4,5-dichlorobenzenesulfonamide), Patent, Aktieselskabet Ferrosan, Ger. 1,135,483, 1962, (2-amino-4,6-dichlorobenzenesulfonamide), H. J. Petersen, Acta Chem. Scand. 27, 2655(1973).

PHARMACOLOGICAL METHODS

The ability of the compounds to interact with potassium channels can be determined by various methods. When patch-clamp techniques (Hamill O. P., Marty A., Neher E., Sakmann B. and Sigworth F. J., *Plügers Arch.*, 391, 85–100 (1981)) are used the ionic current through a single channel of a cell can be recorded.

The activity of the compounds as potassium channel openers can also be measured as relaxation of rat aortas rings according to the following procedure:

A section of rat thoracic aorta between the aortic arch and the diaphragm was dissected out and mounted as ring preparations as described by Taylor P. D. et al, *Brit J. Pharmacol*, 111, 42–48 (1994).

After a 45 min. equilibration period under a tension of 2 g, the preparations were contracted to achieve 80% of the maximum response using the required concentration of phenylephrine. When the phenylephrine response reached a plateau, potential vasodilatory agents were added cumulatively to the bath in small volumes using half log molar increments at 2 min intervals. Relaxation was expressed at the percentage of the contracted tension. The potency of a compound was expressed as the concentration required to evoke a 50% relaxation of the tissue.

| Relaxation of rat aorta rings | |
|---|---|
| Example | EC50 micro M |
| 50 | 5.2 |
| 101 | 14.1 |
| 88 | 32.7 |
| 94 | 4.8 |

In the pancreatic b-cell the opening of the $K_{ATP}$-channels can be determined by measuring the subsequent change in the concentration of cytoplasmic free $Ca^{2+}$ concentration according to the method of Arkhammar P. et al., *J. Biol. Chem.*, 262, 5448–5454 (1987).

$^{86}Rb^+$ efflux from a β-cell line

The RIN 5F cell line was grown in RPMI 1640 with Glutamax I, supplemented with 10% fetal calf serum (from GibcoBRL, Scotland, UK) and maintained in an atmosphere of 5% $CO_2$/95% air at 37° C. The cells were detached with a Trypsin-EDTA solution (from GibcoBRL, Scotland, UK), resuspended in medium, added 1 mCi/ml $^{86}Rb^+$ and replated into microtiter plates (96 well cluster 3596, sterile, from Costar Corporation, MA, USA) at a density of 50000 cells/well in 100 μl/well, and grown 24 hours before use in assay.

The plates were washed 4 times with Ringer buffer (150 mM NaCl, 10 mM Hepes, 3.0 mM KCl, 1.0 mM $CaCl_2$, 20 mM Sucrose, pH 7.1). Eighty μl Ringer buffer and 1 μl control- or test compound dissolved in DMSO was added. After incubation 1 h at room temperature with a lid, 50 μl of the supernatant was transferred to PicoPlates (Packard Instrument Company, CT, USA) and 100 μl MicroScint40

(Packard Instrument Company, CT, USA) added. The plates were counted in TopCount (Packard Instrument Company, CT, USA) for 1 min/well at the $^{32}$P program.

The calculation of $EC_{50}$ and $E_{max}$ was done by SlideWrite (Advanced Graphics Software, Inc., CA, USA) using a four parameter logistic curve: $y=(a-d)/(1+(x/c)^b)+d$, where a=the activity estimated at concentration zero, b=a slope factor, c=the concentration at the middle of the curve and, d=the activity estimated at infinite concentration. $EC_{50}$=c and $E_{max}$=d, when the curve is turned of at infinite concentrations.

| Increased Rb-efflux in rin 5F cells | |
| --- | --- |
| Example | EC50 micro M |
| 26 | 12.9 |
| 66 | 9.4 |
| 86 | 13.0 |

The compounds according to the invention are effective over a wide dosage range. In general satisfactory results are obtained with dosages from about 0.05 to about 1000 mg, preferably from about 0.1 to about 500 mg, per day. A most preferable dosage is about 1 mg to about 100 mg per day. The exact dosage will depend upon the mode of administration, form in which administered, the subject to be treated and the body weight of the subject to be treated, and the preference and experience of the physician or veterinarian in charge.

The route of administration may be any route, which effectively transports the active compound to the appropriate or desired site of action, such as oral or parenteral e.g. rectal, transdermal, subcutaneous, intravenous, intramuscular or intranasal, the oral route being preferred.

Typical compositions include a compound of formula I or a pharmaceutically acceptable acid addition salt thereof, associated with a pharmaceutically acceptable excipient which may be a carrier or a diluent or be diluted by a carrier, or enclosed within a carrier which can be in form of a capsule, sachet, paper or other container. In making the compositions, conventional techniques for the preparation of pharmaceutical compositions may be used.

For example, the active compound will usually be mixed with a carrier, or diluted by a carrier, or enclosed within a carrier which may be in the form of a ampoule, capsule, sachet, paper, or other container. When the carrier serves as a diluent, it may be solid, semi-solid, or liquid material which acts as a vehicle, excipient, or medium for the active compound. The active compound can be adsorbed on a granular solid container for example in a sachet. Some examples of suitable carriers are water, salt solutions, alcohols, polyethylene glycols, polyhydroxyethoxylated castor oil, gelatine, lactose, amylose, magnesium stearate, talc, silicic acid, fatty acid monoglycerides and diglycerides, pentaerythritol fatty acid esters, hydroxymethylcellulose and polyvinylpyrrolidone. The formulations may also include wetting agents, emulsifying and suspending agents, preserving agents, sweetening agents or flavouring agents. The formulations of the invention may be formulated so as to provide quick, sustained, or delayed release of the active ingredient after administration to the patient by employing procedures well known in the art.

The pharmaceutical preparations can be sterilized and mixed, if desired, with auxiliary agents, emulsifiers, salt for influencing osmotic pressure, buffers and/or coloring substances and the like, which do not deleteriously react with the active compounds.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

Generally, the compounds are dispensed in unit form comprising from about 1 to about 100 mg in a pharmaceutically acceptable carrier per unit dosage.

A typical tablet, appropriate for use in this method, may be prepared by conventional tabletting techniques and contains:

| | |
| --- | --- |
| Active compound | 5.0 mg |
| Lactosum | 67.8 mg Ph. Eur. |
| Avicel ® | 31.4 mg |
| Amberlite ® | 1.0 mg |
| Magnesii stearas | 0.25 mg Ph. Eur. |

EXAMPLES

The process of preparing the compounds of formula I is further illustrated in the following examples which, however, are not to be construed as limiting.

General Procedures for the Preparation of the 3-alkylamino-4H-1,2,4-benzothiadiazine 1,1-dioxides Method A A mixture of the appropriate 3-methylsulfanyl-substituted or 3-(imidazol-1-yl)-substituted benzothiadiazine 1,1-dioxide (0.5 g) and the appropriate alkylamine (5 mL) was heated in a sealed vessel at 120–150° C. for 4–8 h (until completion of the reaction monitored by t.l.c.). The excess of amine was removed by distillation under reduced pressure and the oily residue was dispersed in water. The suspension was supplemented with 2.5N NaOH until complete dissolution. The resulting solution was treated with charcoal, filtered, and the filtrate was adjusted to pH 5–6 with 6N HCl. The precipitate was collected by filtration, washed with water and recrystallized from methanol-water (yields: 60–90%).

Method B

A mixture of the appropriate 3-methylsulfanyl-substituted or 3-(imidazol-1-yl)-substituted benzothiadiazine 1,1-dioxide (0.5 g) and the appropriate alkylamine (5 mL) was refluxed for 2–120 h (until completion of the reaction monitored by t.l.c.). The final compound was then isolated and purified as reported in method A (yields: 60–90%).

Method C

A mixture of the appropriate 3-methylsulfanyl-substituted or 3-(imidazol-1-yl)-substituted benzothiadiazine 1,1-dioxide (0.5 g) and the appropriate alkylamine (1 mL) in 3-chlorotoluene (5 mL) was refluxed for 1–3 h (until completion of the reaction monitored by t.l.c.). Most of the solvent and the excess of amine was removed by distillation, and the oily residue was dispersed in a 1:1 mixture of methanol and water (50–100 mL). A 10% aqueous solution of NaOH was added dropwise until dissolution of most of the insoluble material. The alkaline medium was treated with charcoal, filtered, and the filtrate was adjusted to pH 5–6. The precipitate was collected by filtration, washed with water and recrystallized from methanol-water (yields: 60–90%).

Method D

A mixture of the appropriate 3-methylsulfanyl-substituted or 3-(imidazol-1-yl)-substituted benzothiadiazine 1,1-dioxide (0.6 g) and the appropriate alkylamine (1 mL) in dioxane (5 mL) was heated in a sealed vessel at 120–150° C. for 4–8 h (until completion of the reaction monitored by t.l.c.). The final compound was then isolated and purified as reported in method A (yields: 60–90%).

Example 1

7-Chloro-3-(2-phenylethyl)amino-4H-1,2,4-benzothiadiazine 1,1-dioxide

2-Phenylethyl isothiocyanate (0.36 g) was added to a stirred slurry of 2-amino-5-chlorobenzenesulfonamide sodium salt (0.50 g) in 5 ml of acetonitrile at 60° C. After 2½ h an additional amount of 2-phenylethyl isothiocyanate (0.18 g) was added, and the temperature was raised to 90° C. for 1½ h. The reaction mixture was treated with 1 ml of 4M acetic acid, 5 ml of ethanol and 0.1 g of charcoal and filtered through celite. The solvent was evaporated and the residue extracted with 10 ml of ethyl acetate. The solvent was evaporated and the oily residue was purified on a silica column eluted with ethyl acetate. The title compound was obtained as white crystals; m.p. 250–252° C.

Example 2

7-Bromo-3-isopropylamino-4H-1,2,4-benzothiadiazine 1,1-dioxide

To a suspension of 2-amino-5-bromobenzenesulfonamide (0.8 g; 3.2 mmol) and potassium carbonate (0.54 g; 3.9 mmol) in acetone (20 ml) was added isopropyl isothiocyanate (0.387 g; 3.84 mmol). The mixture was heated to 60° C. and after 16 hr cooled, concentrated in vacuo and the crude residue was taken up in tetrahydrofuran (50 ml) and cooled to 0° C. To the cooled mixture was added triethylamine (0.648 g; 6.4 mmol) followed by the addition of phosgene in toluene 1.9M (1.82 ml) over 2 min. After 1 hr at 0° C. the mixture was concentrated in vacuo. The crude product was taken up in water (10 ml) and pH was adjusted to 6 with sodium bicarbonate. The precipitated product was collected by filtration and dried in vacuo at 50° C. for 16 hr giving 390 mg (38.3%) of the title compound; m.p. >220° C.

$^1$H-NMR (DMSO-d6) ppm; 10.49 (br s, 1H, NH), 7.75 (m, 2H, H-6 and H-8), 7.21 (s, 1H, H-5), 7.15 (s, 1H, NH), 3.97 (m, 1H, CH) 1.19 (d, 6H, 2×CH$_3$).

Example 3

6,8-Dichloro-3-isopropylamino-4H-1,2,4-benzothiadiazine 1,1-dioxide

A mixture of 2-amino-4,6-dichlorobenzenesulfonamide (1.0 g), isopropyl isothiocyanate (0.84 g), copper(l) chloride (0.4 g), and DMF (1.5 ml) was heated at 100° C. for 2 h. Then 5 ml of methanol was added and the precipitated material was removed by filtration. Evaporation of the solvent in vacuo and subsequent treatment of the residue with 25 ml of ethyl acetate gave a yellow precipitate, which was collected by filtration and recrystallized from ethanol to give the title compound as white crystals; m.p. 291–293° C.

Example 4

3-Isopropylamino-6-methanesulfonyl-4H-1,2,4-benzothiadiazine 1,1-dioxide
a) N-(2-amino-4-(methanesulfonyl)benzenesulfonyl)-N'-isopropylthiourea
A mixture of 2-amino-4-methanesulfonylbenzenesulfonamide (2.5 g), potassium carbonate (1.66 g) and isopropyl isothiocyanate (1.22 g) in 20 ml of dry acetone was heated at 50° C. for 18 h. Then the reaction mixture was evaporated in vacuo and the residue was dissolved in 25 ml of water. Then the solution was adjusted to pH 2 by dropwise addition of 4 M HCl at 0° C. with stirring. After stirring for 2 h the product was filtered off and dried, yielding the title compound as white crystals; m.p. 151–153° C.
b) 3-Isopropylamino-6-methanesulfonyl-4H-1,2,4-benzothiadiazine 1,1-dioxide To a stirred mixture of N-(2-amino-4-(methanesulfonyl) benzenesulfonyl)-N'-isopropylthiourea (3.0 g) and triethylamine (1.7 g) in 30 ml of dry THF at 0° C. was added 5.2 ml of a 20% solution of phosgene in toluene during 5 min. The mixture was stirred at 0° C. for 1 h and then evaporated in vacuo. The white, solid residue was triturated with 50 ml of water for 45 min. and then the product was isolated by filtration. The filter cake was rinsed on the filter with water and dried to give the title compound as white crystals; m.p. >300° C.

$^1$H-NMR(d$_6$-DMSO)), δ (ppm): 10.7 (br, 1H, NH), 7.98–7.72 (m, 3H, arom.), 7.43 (br, 1H, NH), 4.07–3.87 (m, 1H, CH), 3.29 (s, 3H, CH$_3$), 1.20 (d, 6H, CH$_3$).

Example 5

3-Isopropylamino-6-benzenesulfonyl-4H-1,2,4-benzothiadiazine 1,1-dioxide

Starting from 2-amino-4-(benzenesulfonyl) benzenesulfonamide and isopropyl isothiocyanate, and following a procedure analogous to the one described in Example 4a, N-(2-amino-4-(benzenesulfonyl) benzenesulfonyl)-N'-isopropylthiourea was prepared; m.p. 178–180° C. Subsequent ring closure with phosgene by a procedure analogous to the one described in Example 4b gave the title compound, m.p. 308–310° C.

Example 6

5-Chloro-3-isopropylamino-4H-1,2,4-benzothiadiazine 1,1-dioxide

Starting from 2-amino-4-methylbenzenesulfonamide and isopropyl isothiocyanate, and following a procedure analogous to the one described in Example 4a, N-(2-amino-3-chlorobenzenesulfonyl)-N'-isopropylthiourea was prepared; m.p. 124–125° C. Subsequent ring closure with phosgene by a procedure analogous to the one described in Example 4b gave the title compound; m.p. 204–206° C.

Example 7

3-Isopropylamino-6-methyl-4H-1,2,4-benzothiadiazine 1,1-dioxide

Starting from 2-amino-4-methylbenzenesulfonamide and isopropyl isothiocyanate, and following a procedure analogous to the one described in Example 4a, N-(2-amino-4-methylbenzenesulfonyl)-N'-isopropylthiourea was prepared, m.p. 137–139° C. Subsequent ring closure with phosgene by a procedure analogous to the one described in Example 4b gave the title compound; m.p. 309–311° C.

Example 8

6-Chloro-3-isopropylamino-7-methyl-4H-1,2,4-benzothiadiazine 1,1-dioxide

Starting from 2-amino-4-chloro-5-methylbenzenesulfonamide and isopropyl isothiocyanate, and following a procedure analogous to the one described in Example 4a, N-(2-amino-4-chloro-5-methylbenzenesulfonyl)-N'-isopropylthiourea was prepared; m.p. 120–122° C. Subsequent ring closure with phosgene by a procedure analogous to the one described in Example 4b gave the title compound; $^1$H-NMR (d$_6$-DMSO), δ (ppm): 10.3 (br, 1H, NH), 7.68 (1H, arom.), 7.29 (1H, arom), 7.2 (br, 1H, NH), 4.0–3.8 (m, 1H, CH), 2.37 (s, 3H, CH$_3$), 1.20 (d, 6H, CH$_3$).

Example 9

Ethyl (3-Isopropylamino-1,1-dioxo-1,4-dihydro-1λ$^6$,2,4-benzothiadiazin-6-yl)acetate Starting from ethyl 3-amino-4-sulfamoylphenylacetate and isopropyl isothiocyanate, and following a procedure analogous to the one described in Example 4a, N-(2-amino-3-(ethoxycarbonylmethyl)benzenesulfonyl)-N'-isopropylthiourea was prepared; m.p. 111–112° C.

Subsequent ring closure with phosgene by a procedure analogous to the one described in Example 4b gave the title compound; m.p. 182–184° C.; $^1$H-NMR (d$_6$-DMSO), δ (ppm): 10.4 (s, 1H, NH), 7.65–7.57 (1H, arom.), 7.2–7.03 (m, 3H, arom.), 7.03–6.9 (br, 1H, NH), 4.18–401 (q, 2H, CH$_2$), 4.01–3.8 (m, 1H, CH), 3.77 (s, 2H, CH$_2$), 1.25–1.1 (t+d, 9H, CH$_3$).

Example 10

8-Chloro-3-isopropylamino-4H-1,2,4-benzothiadiazine 1,1-dioxide

Starting from 2-amino-6-chlorobenzenesulfonamide and isopropyl isothiocyanate, and following a procedure analogous to the one described in Example 4a, N-(2-amino-6-chlorobenzenesulfonyl)-N'-isopropylthiourea was prepared; m.p. 144–146° C. Subsequent ring closure with phosgene by a procedure analogous to the one described in Example 4b gave the title compound; m.p. 273–275° C.

Example 11

6-Isopropyl-3-isopropylamino-4H-1,2,4-benzothiadiazine 1,1-dioxide

Starting from 2-amino-4-isopropylbenzenesulfonamide and isopropyl isothiocyanate, and following a procedure analogous to the one described in Example 4a, N-(2-amino-4-isopropylbenzenesulfonyl)-N'-isopropylthiourea was prepared. The crude product containing approx. 16% starting material (by $^1$H-nmr) was used without purification for the next step. Subsequent ring closure with phosgene by a procedure analogous to the one described in Example 4b gave the title compound; m.p. 237–239° C.

Example 12

7-tert-Butyl-3-isopropylamino-4H-1,2,4-benzothiadiazine 1,1-dioxide

Starting from 2-amino-5-tert-butylbenzenesulfonamide and isopropyl isothiocyanate, and following a procedure analogous to the one described in Example 4a, N-(2-amino-5-tert-butylbenzenesulfonyl)-N'-isopropylthiourea was prepared; m.p. 128–130° C. Subsequent ring closure with phosgene by a procedure analogous to the one described in Example 4b gave the title compound; m.p. 290–293° C.

Example 13

3-Isopropylamino-6-phenoxy-4H-1,2,4-benzothiadiazine 1,1-dioxide

Starting from 2-amino-4-phenoxybenzenesulfonamide and isopropyl isothiocyanate, and following a procedure analogous to the one described in Example 4a, N-(2-amino-4-phenoxybenzenesulfonyl)-N'-isopropylthiourea was prepared. The impure crude product was used without purification. Subsequent ring closure with phosgene by a procedure analogous to the one described in Example 4b gave the title compound; m.p. 250–252° C.

Example 14

6-Hexyl-3-isopropylamino-4H-1,2,4-benzothiadiazine 1,1-dioxide

Starting from 2-amino-4-hexylbenzenesulfonamide and isopropyl isothiocyanate, and following a procedure analogous to the one described in Example 4a, N-(2-amino-4-hexylbenzenesulfonyl)-N'-isopropylthiourea was prepared. The crude product was obtained as an oil and used without purification. Subsequent ring closure with phosgene by a procedure analogous to the one described in Example 4b gave the title compound; m.p. 319–321° C.

Example 15

6-Cyclohexyl-3-isopropylamino-4H-1,2,4-benzothiadiazine 1,1-dioxide

Starting from 2-amino-4-cyclohexylbenzenesulfonamide and isopropyl isothiocyanate, and following a procedure analogous to the one described in Example 4a, N-(2-amino-4-cyclohexylbenzenesulfonyl)-N'-isopropylthiourea was prepared; m.p. 131–133° C. Subsequent ring closure with phosgene by a procedure analogous to the one described in Example 4b gave the title compound; m.p. 264–266° C.

Example 16

6-Chloro-3-(1-ethylpropyl)amino-4H-1,2,4-benzothiadiazine 1,1-dioxide

The title compound was prepared from 2-amino-4-chlorobenzenesulfonamide and 3-pentyl isothiocyanate by a method analogous to the one described in Example 4; m.p. 224–226° C. (ethyl acetate); $^1$H-NMR (DMSO-d$_6$): δ 0.88 (t, 6H, 2×CH$_3$), 1.33–1.66 (m, 4H, 2×CH$_2$), 3.65 (m, 1H, CH), 7.1 (br.s, 1H, NH), 7.21–7.32 (m, 2H, ArH), 7.68 (d, 1H, ArH), 10.30 (br.s, 1H, NH); MS: m/e 301–303 (M+); (C$_{12}$H$_{16}$N$_3$Cl$_1$O$_2$S$_1$) calc. C, 47.76; H, 5.34; N, 13.92; found C, 47.74; H, 5.49; N, 13.93.

Example 17

(3-Isopropylamino-1,1-dioxo-1,4-dihydro-1λ$^6$,2,4-benzothiadiazin-6-yl)acetic acid Ethyl (3-isopropylamino-1,1-dioxo-1,4-dihydro-1λ$^6$,2,4-benzothiadiazin-6-yl)acetate (0.22 g) was stirred in 5 ml of 4M aqueous sodium hydroxide at room temperature for 1 h. The reaction mixture was then acidified with 4M hydrochloric acid. The resulting precipitate was collected by filtration, the filter cake was rinsed with a small amount of water and dried to give 0.17 g of the title compound, m.p. 262–264° C.

Example 18

6-(3-Cyclopropyl-1,2,4-oxadiazol-5-yl)methyl-3-isopropylamino-4H-1,2,4-benzothiadiazine 1,1-dioxide A mixture of ethyl (3-isopropylamino-1,1-dioxo-1,4-dihydro-1λ$^6$,2,4-benzothiadiazin-6-yl)acetate (0.20 g), crushed 4 Å molecular sieves (0.6 g), cyclopropanecarboxamide oxime (0.30 g), and sodium hydride (40 mg of a 60% oil dispersion) in 5 ml of dry dimethylformamide was stirred at room temperature for 45 min. Two drops of glacial acetic acid and 20 ml of dichloromethane were added and the mixture was stirred for 10 min. and filtered through celite. The solvents were removed in vacuo from the filtrate. The remaining oil was stirred with 5 ml of water for 15 min and the resulting precipitate was collected by filtration and dried to give the title compound; m.p. 255–259° C.

Example 19

2-(3-Isopropylamino-1,1-dioxo-1,4-dihydro-1$\lambda^6$,2,4-benzothiadiazin-6-yl)acetamide Ammonia gas was passed through a solution of ethyl (3-isopropylamino-1,1-dioxo-1,4-dihydro-1$\lambda^6$,2,4-benzothiadiazin-6-yl)acetate (0.20 g) and sodium cyanide (20 mg) in 10 ml of methanol at room temperature for 5 min. The solution was heated at 55–60° C. in a sealed flask overnight. The solvent was removed in vacuo and the residue was treated with 25 ml of water. On standing, a crystalline precipitate was formed. The crystals were filtered off and dried to give the title compound; m.p. 321–325° C.

Example 20

(3-Isopropylamino-1,1-dioxo-1,4-dihydro-1$\lambda^6$,2,4-benzothiadiazin-6-yl)acetonitrile A slurry of 2-(3-isopropylamino-1,1-dioxo-1,4-dihydro-1$\lambda^6$,2,4-benzothiadiazin-6-yl)acetamide (50 mg) in a mixture of 0.8 ml of acetonitrile, 0.2 ml of formic acid and 25 mg of paraformaldehyde was heated at reflux for 16 h, and then evaporated to dryness. The residue was purified on a silica column eluted with dichloromethane-methanol (95:5) to give the title compound; m.p. 195–203° C.

Example 21

3-Benzyloxyamino-7-chloro-4H-1,2,4-benzothiadiazine 1,1-dioxide

To a solution of O-benzylhydroxylamine hydrochloride (500 mg) and triethylamine (200 mg) in ethanol (10 ml) was added 3,7-dichloro-4H-1,2,4-benzothiadiazine 1,1-dioxide (500 mg). The mixture was stirred for 3 h and concentrated in vacuo. The crude product was taken up in hot ethyl acetate (50 ml) and cooled to room temperature and the precipitate was collected by filtration to give the title compound (200 mg, 59%); m.p. >220° C.; $^1$H-NMR (DMSO-d6) ppm; 11.2 (br s, 1H, NH), 7.7–7.35 (m, 9H, arom. and NH), 4.49 (s, 2H, CH$_2$). Analysis: $C_{14}H_{12}ClN_3O_3S$ requires C, 49.78; H, 3.58; N, 12.44; (found C, 49.49; H, 3.80; N, 12.09).

Example 22

7-Chloro-3-methoxyamino-4H-1,2,4-benzothiadiazine 1,1-dioxide

Starting from 3,7-dichloro-4H-1,2,4-benzothiadiazine 1,1-dioxide (502 mg; 2 mmol) and O-methylhydroxylamine hydrochloride (300 mg) and with the use of the same procedure as in example 21, 280 mg (57%) of the title compound was prepared; m.p. >220° C.; $^1$H-NMR (DMSO-d6) ppm; 11.35 (s, 1H, NH), 11.28 (s, 1H, NH), 7.78 (d, 1H, H-8), 7.63 (dd, 2H, H-6 and H-5), 3.80 (s, 3H, CH$_3$); $^{13}$C-NMR (DMSO-d6) ppm; 151.19, 132.79, 131.26, 127.10, 123.00, 120.83, 118.78, 63.25.

Example 23

6-Chloro-3-butylamino-4H-1,2,4-benzothiadiazine 1,1-dioxide

The title compound was prepared from 2-amino-4-chlorobenzenesulfonamide and butyl isothiocyanate by a method analogous to the one described in Example 4; m.p. 267–269° C. (ethyl acetate); $^1$H-NMR (DMSO-d$_6$): δ 0.90 (t, 3H, CH$_3$), 1.24–1.60 (m, 4H, CH$_2$CH$_2$), 3.21 (q, 2H, NHCH$_2$), 7.2–7.4 (m, 3H, ArH+NH), 7.68 (d, 1H, ArH), 10.55 (br.s, 1H, NH); MS: m/e 287–289 (M+); ($C_{11}H_{14}N_3Cl_1O_2S_1$) calc. C, 45.91; H, 4.91; N, 14.60; found C, 45.92; H, 5.12; N, 14.46.

Example 24

6-Chloro-3-hexylamino-4H-1,2,4-benzothiadiazine 1,1-dioxide

The title compound was prepared from 2-amino-4-chlorobenzenesulfonamide and hexyl isothiocyanate by a method analogous to the one described in Example 4; m.p. 244–247° C. (ethyl acetate); $^1$H-NMR (DMSO-d$_6$): δ 0.88 (distorted t, 3H, CH$_3$), 1.31 (m, 6H, 3×CH$_2$), 1.53 (m, 2H, CH$_2$), 3.22 (q, 2H, NHCH$_2$), 7.2–7.4 (m, 3H, ArH+NH), 7.68 (d, 1H, ArH), 10.55 (br.s, 1H, NH); MS: m/e 315/317 (M+); ($C_{13}H_{18}N_3Cl_1O_2S_1$) caic. C, 49.44; H, 5.74 N, 13.31; found C, 49.59; H, 6.01; N, 13.25.

Example 25

7-Bromo-3-isopropylamino-6-trifluoromethyl-4H-1,2,4-benzothiadiazine 1,1-dioxide A solution of 3-isopropylamino-6-trifluoromethyl-4H-1,2,4-benzothiadiazine 1,1-dioxide (307 mg; 1 mmol) in water (5 ml) was added 40% hydrobromic acid (0.44 ml; 3 mmol). The solution was then heated to 70° C. and 30% hydrogen peroxide (0.33 g; 3 mmol) was added. After 30 min the reaction mixture was cooled and extracted with ethyl acetate (20 ml) and purified by column chromatograpy (ethyl acetate:ethanol 9:1). Concentration of the appropiate fractions produced the title compound (22 mg); $^1$H-NMR (DMSO-d6) ppm; 7.60 (s, 1H), 7.10 (s, 1H), 6.65 (s, 1H), 3.95 (m, 1H) 1.11 (d, 6H).

Example 26

6,7-Dichloro-3-(1,2-dimethylpropyl)amino-4H-1,2,4-benzothiadiazine 1,1-dioxide

The title compound was prepared from 2-amino-4,5-dichlorobenzenesulfonamide and 1,2-dimethylpropyl isothiocyanate by a method analogous to the one described in Example 4; m.p. 242–250° C. (ethyl acetate); $^1$H-NMR (DMSO-d$_6$): δ 0.90 (d, 3H, CH$_3$), 0.91 (d, 3H, CH$_3$), 1.10 (d, 1H, CH$_3$), 1.77 (m, 1H, CH(CH$_3$)$_2$), 3.71 (m, 1H, NHCH), 7.29 (br., 1H, NH), 7.49 (br.s, 1H, ArH), 7.89 (s, 1H, ArH), 10.41 (br.s, 1H, NH); MS: m/e 335/337/339 (M+); ($C_{12}H_{15}N_3Cl_2O_2S_1$) calc. C, 42.87; H, 4.50; N, 12.50; found C, 42.94; H, 4.68; N, 12.45.

Example 27

6-Chloro-3-(1,2,2-trimethylpropyl)amino-4H-1,2,4-benzothiadiazine 1,1-dioxide

Starting from 3,6-dichloro-4H-1,2,4-benzothiadiazine 1,1-dioxide (500 mg; 1.99 mmol) and 1,2,2- trimethylpropylamine (500 mg; 5.62 mmol) with the use of same procedure as in example 21 250 mg (39.8%) of the title compound was prepared; m.p. >220° C.; $^1$H-NMR (DMSO-d6) ppm; 10.3 (s, 1H, NH), 7.70 (d, 1H, H-8), 7.31 (dd, 1H, H-7), 7.25 (br d, 1H, H-5), 7.15 (br, 1H, NH), 3.75 (q, 1H, CH), 1.10 (d, 3H, CH$_3$), 0.9 (s, 9H, 3×CH$_3$). Analysis: C$_{13}$H$_{18}$ClN$_3$O$_2$S requires C, 49.44; H, 5.74; N, 13.3; (found C, 49.37; H, 6.04; N, 13.11).

Example 28

7-Bromo-3-(1,2,2-trimethylpropyl)amino-4H-1,2,4-benzothiadiazine 1,1-dioxide

Starting from 7-bromo-3-chloro-4H-1,2,4-benzothiadiazine 1,1-dioxide (300 mg; 1.01 mmol) and 1,2,2-trimethylpropylamine (359 mg; 4.04 mmol) with the use of same procedure as in example 21 200 mg (54.9%) of the title compound was prepared; m.p. >220° C.; $^1$H-NMR (DMSO-d6) ppm; 10.35 (s, 1H, NH), 7.78 (d, 1H, H-8), 7.6 (dd, 1H, H-6), 7.12 (br d, 1H, H-5), 6.95 (br, 1H, NH), 3.72 (q, 1H, CH), 1.10 (d, 3H, CH$_3$), 0.92 (s, 9H, 3×CH$_3$); MS:EI/70eV: 361 (M+1), 304, 277, 236, 170, 116, 90, 44.

Example 29

6,7-Dichloro-3-(1-methylbutyl)amino-4H-1,2,4-benzothiadiazine 1,1-dioxide

The title compound was prepared from 2-amino-4,5-dichlorobenzenesulfonamide and 2-pentyl isothiocyanate by a method analogous to the one described in Example 4; m.p. 217–220° C. (ethyl acetate); $^1$H-NMR (DMSO-d$_6$): δ 0.90 (t, 3H, CH$_3$), 1.14 (d, 3H, CH$_3$), 1.20–1.55 (m, 4H, CH$_2$CH$_2$), 3.83 (m, 1H, NHCH), 7.33 (br., 1H, NH), 7.49 (br.s, 1H, ArH), 7.89 (s, 1H, ArH), 10.48 (br.s, 1H, NH); MS: m/e 335/337/339 (M+).

Example 30

5-Amino-7-chloro-3-isopropylamino-4H-1,2,4-benzothiadiazine 1,1-dioxide

To a stirred suspension of 7-chloro-3-isopropylamino-5-nitro-4H-1,2,4-benzothiadiazine 1,1-dioxide (200 mg; 0.63 mmol) and zink (200 mg; 3.06 mmol) in acetic acid (20 ml) was added 36% hydrochloric acid (0.3 ml). The mixture was stirred for 12 hr. After filtration and concentation in vacuo the crude product was purified by column chromatography eluting with ethyl acetate:ethanol (9:1). Concentration of the appropriate fractions produced 90 mg of the title compound; m.p. >230° C.

Example 31

7-Chloro-3-(1,3-dimethylpentyl)amino-4H-1,2,4-benzothiadiazine 1,1-dioxide

Starting from 3,7-dichloro-4H-1,2,4-benzothiadiazine 1,1-dioxide (500 mg; 1.99 mmol) and 1,3-dimethylpentylamine (1 g; 8.68 mmol) and with the use of same procedure as in example 21 230 mg (35.1%) of the title compound was prepared; m.p. >220° C.; $^1$H-NMR (DMSO-d6) ppm; 10.41 (s, 1H, NH), 7.68 (d, 1H, H-8), 7.60 (dd, 1H, H-5), 7.2 (d, 1H, H-7), 7.0 (br, 1H, NH), 3.95 (m, 1H, CH), 1.5 (m, 8H), 0.9 (m, 6H, 2×CH$_3$); MS:EI/70eV: 329 (M+), 301, 258, 231, 190, 126, 69, 44. Analysis: C$_{14}$H$_{20}$ClN$_3$O$_2$S requires C, 50.98; H, 6.11; N, 12.74; (found C, 51.23; H, 6.42; N, 12.53).

Example 32

7-Chloro-3-(1,5-dimethylhexyl)amino-4H-1,2,4-benzothiadiazine 1,1-dioxide

Starting from 3,7-dichloro-4H-1,2,4-benzothiadiazine 1,1-dioxide (300 mg; 1.19 mmol) and 1,5-dimethylhexylamine (1 g; 7.73 mmol) and with the use of same procedure as in example 21 260 mg (63.5%) of the title compound was prepared; m.p. >220° C.; $^1$H-NMR (DMSO-d6) ppm; 10.50 (s, 1H, NH), 7.68 (d, 1H, H-8), 7.63 (dd, 1H, H-5), 7.25 (d, 1H, H-7), 7.1 (br, 1H, NH), 3.85 (q, 1H, CH), 1.5 (m, 4H ), 1.35 (m, 3H ), 1.15 (d, 3H, CH$_3$), 0.85 (d, 6H, 2×CH$_3$).

MS:EI/70eV: 343 (M$^+$), 300, 258, 231, 190, 126, 69, 44.

Example 33

7-Chloro-3-(1,4-dimethylpentyl)amino-4H-1,2,4-benzothiadiazine 1,1-dioxide

Starting from 3,7-dichloro-4H-1,2,4-benzothiadiazine 1,1-dioxide (300 mg; 1.19 mmol) and 1,4-dimethylpentylamine (1.0 g; 8.68 mmol) with the use of same procedure as in example 21 210 mg (53.5%) of the title compound was prepared; m.p. >220° C.; $^1$H-NMR (DMSO-d6) ppm; 10.4 (s, 1H, NH), 7.7 (d, 1H, H-8), 7.6 (dd, 1H, H-5), 7.25 (d, 1H, H-7), 7.1 (br, 1H, NH), 3.88 (q, 1H, CH$_2$), 1.55 (m, 3H), 1.21 (m, 2H), 1.1 (d, 3H, CH$_3$), 0.9 (d, 6H, 2×CH$_3$); MS:EI/70eV: 330 (M$^+$), 258, 231, 190, 126, 69, 55, 44. Analysis: C$_{10}$H$_{12}$ClN$_3$O$_2$S requires C, 50.98; H, 6.11; N, 12.74; (found C, 51.14; H, 6.43; N, 12.64)

Example 34

5,7-Dichloro-3-isopropylamino-4H-1,2,4-benzothiadiazine 1,1-dioxide

Starting from 2-amino-3,5-dichlorobenzenesulfonamide (0.5 g; 2.07 mmol) and isopropyl isothiocyanate (251 mg; 2.48 mmol) with the use of the procedure described in example 4, 100 mg (17.4%) of the title compound was isolated; m.p. >230° C.

Example 35

7-Chloro-3-(3,3-diphenylpropylamino)-4H-1,2,4-benzothiadiazine 1,1-dioxide

Starting from 3,7-dichloro-4H-1,2,4-benzothiadiazine 1,1-dioxide (300 mg; 1.19 mmol) and 3,3-diphenylpropylamine (1.5 g; 7.1 mmol) with the use of same procedure as in example 21 300 mg (59%) of the title compound was prepared; $^1$H-NMR (DMSO-d6) ppm; 10.7 (s, 1H, NH), 7.68 (d, 1H, H-8), 7.60 (dd, 1H, H-5), 7.25 (m, 11H, ), 4.1 (t, 1H, CH), 3.11 (q, 2H, CH$_2$), 2.35 (q, 2H, CH$_2$); MS:EI/70eV: 425 (M+), 245, 193, 180, 165, 152, 115.

Example 36

7-Chloro-3-(4-phenylbutylamino)-4H-1,2,4-benzothiadiazine 1,1-dioxide

Starting from 3,7-dichloro-4H-1,2,4-benzothiadiazine 1,1-dioxide (300 mg; 1.19 mmol) and 4-phenylbutylamine (1.5 g; 4.12 mmol) and with the use of same procedure as in example 21 120 mg (27.7%) of the title compound was prepared.; $^1$H-NMR (DMSO-d6) ppm; 10.8 (s, 1H, NH), 7.75 (d, 1H, H-8), 7.60 (dd, 1H, H-5), 7.2 (m, 7H), 3.29 (t, 2H, CH$_2$), 2.66 (t, 2H, CH$_2$), 1.5 (m, 4H, 2×CH$_2$); MS:EI/70eV: 363 (M$^+$), 272, 259, 231, 180, 91, 44.

Example 37

6-Chloro-3-(1,2-dimethylpropyl)amino-4H-1,2,4-benzothiadiazine 1,1-dioxide

Phosphorus pentoxide (7.55 g, 53.2 mmol), N,N-dimethylcyclohexylamine (17 ml, 113 mmol) and 1,2- dimethylpropylamine hydrochloride (12.4 g, 100.4 mmol) were carefully mixed and heated with mechanical stirring on an oil bath at 190–200° C. for about 15 min. To the homogeneous mass was added 6-chloro-3,4-dihydro-3-oxo-1,2,4-benzothiadiazine 1,1-dioxide (5.84 g, 25.1 mmol) and the mixture was stirred at 235° C. for 2 h. After cooling to about 100° C., water (200 ml) was added and the dark mixture was hydrolysed by stirring over night at room temperature. The precipitate was isolated by filtration and recrystallised from ethanol with decolorising charcoal to give 2,83 g (37%) of the pure title compound; m.p. (DSC) 264.7° C.; $^1$H-NMR (DMSO-d$_6$): δ 0.90 (dd, 6H, CH(CH$_3$)$_2$), 1.09 (d, 3H, NCHCH$_3$), 1.76 (m, 1H, CH(CH$_3$)$_2$), 3.70 (m, 1H, NHCH), 7.15 (br., 1H, NH), 7.28 (m, 2H, ArH), 7.68 (d, 1H, ArH), 10.3 (br.s, 1H, NH); (C$_{12}$H$_{16}$N$_3$Cl$_1$O$_2$S$_1$) calc. C, 47.76; H, 5.34; N 13.92; found C, 47.66; H, 5.47; N, 13.91.

Example 38

6-Chloro-3-(1,2-dimethylpropyl)amino-7-sulfamoyl-4H-1,2,4-benzothiadiazine 1,1-dioxide The title compound was prepared from 6-chloro-2,3-dihydro-3-oxo-7-sulfamoyl-1,2,4-benzothiadiazine 1,1-dioxide (4.94 g, 15.84 mmol) and 1,2-dimethylpropylamine hydrochloride (8.0 g, 65.0 mmol) by a method analogous to the method described in example 37, except that the product was purified by column chromatography affording 143 mg (2.4%) of pure product; m.p. (DSC) 244° C. (methanol); $^1$H-NMR (DMSO-d$_6$): δ 0.90 (dd, 6H, CH(CH$_3$)$_2$), 1.11 (d, 3H, NCHCH$_3$), 1.76 (m, 1H, CH(CH$_3$)$_2$), 3.71 (m, 1H, NHCH), 7.34 (br., 1H, NH), 7.41 (br.s, 1H, ArH), 7.80 (br.s, 2H, SO$_2$NH$_2$), 8.18 (s, 1H, ArH), 10.58 (br.s, 1H, NH); MS (FAB): m/e 381/383 (MH+); (C$_{12}$H$_{17}$N$_4$Cl$_1$O$_4$S$_2$) calc. C, 37.84; H, 4.50; N, 14.71; found C, 37.66; H, 4.65; N, 14.52.

Example 39

3-Anilino-7-chloro-4H-1,2,4-benzothiadiazine 1,1-dioxide

The title compound was prepared from 6-chloro-2,3-dihydro-3-oxo-1,2,4-benzothiadiazine 1,1-dioxide (3.0 g, 12.9 mmol) and aniline (4.8 g, 52.0 mmol) by a method analogous to the method described in example 37, except that triethylamine hydrochloride (7.1 g, 52.0 mmol) was used instead of N,N-dimethylcyclohexylamine. Yield 1.68 g (44%) of pure product; m.p. (DSC) >350° C. (ethanol); $^1$H-NMR (DMSO-d$_6$): δ 7.1–7.8 (m, 8H, ArH), 9.5 (br.s, 1H, NH), 11.05 (br.s, 1H, NH,; MS: m/e 307/309 (M+); (C$_{13}$H$_{10}$N$_3$Cl$_1$O$_2$S$_1$) calc. C, 50.74; H, 3.28; N, 13.65; found C, 50.31; H, 3.24; N, 13.59.

Example 40

7-Chloro-3-(4-pyridyl)amino-4H-1,2,4-benzothiadiazine 1,1-dioxide

The title compound was prepared from 6-chloro-2,3-dihydro-3-oxo-1,2,4-benzothiadiazine 1,1-dioxide (3.0 g, 12.9 mmol) and 4-aminopyridine (4.9 g, 52.0 mmol) by a method analogous to the method described in example 39, except that the hydrolysed mixture was adjusted to pH 7 and extracted with ethyl acetate (5×50 ml).The organic phase was evaporated to dryness and the residue was purified by column chromatography affording 34 mg (0.9%) of product; $^1$H-NMR (DMSO-d$_6$): δ 7.32 (d, 1H, ArH), 7.40–7.52 (m, 4H, ArH), 7.68 (dd, 1H, ArH), 7.76 (dd, 1H, ArH), 9.6 (br.s, 1H, NH), 11.05 (br s, 1H, NH).

Example 41

6-Chloro-3-isobutylamino-4H-1,2,4-benzothiadiazine 1,1-dioxide

A mixture of 2-amino-4-chlorobenzenesulfonamide (5.0 g, 24.18 mmol) and isobutyl isothiocyanate (10 ml, 83.6 mmol) was heated at 150° C. for 3 h. The mixture was allowed to cool and then stirred with 50 ml of ethyl acetate for 30 min. The precipitate was isolated by filtration and recrystallised from ethanol to give 2.9 g (42%) of the pure title compound; m.p. 298–301° C.; $^1$H-NMR (DMSO-d$_6$): δ 0.91 (d, 6H, CH(CH$_3$)$_2$), 1.83 (m, 1H, CH(CH$_3$)$_2$), 3.05 (t, 2H, CH$_2$), 7.2–7.4 (m, 3H, ArH+NH), 7.67 (d, 1H, ArH), 10.5 (br.s, 1H, NH); MS: m/e 287/289 (M+); (C$_{11}$H$_{14}$N$_3$Cl$_1$O$_2$S$_1$) calc. C, 45.91; H, 4.90; N, 14.60; found C, 45.90; H, 5.04; N, 14.66.

Example 42

3-sec-Butylamino-6-chloro-4H-1,2,4-benzothiadiazine 1,1-dioxide

A mixture of 2-amino-4-chlorobenzenesulfonamide (2.1 g, 10.16 mmol) and sec-butyl isothiocyanate (5.0 ml, 40.9 mmol) was heated at 150° C. for 4 h. The mixture was allowed to cool and then stirred with 25 ml of ethyl acetate for 1 h. The precipitate was isolated by filtration and recrystallised from ethanol to give 201 mg (7%) of the title compound as white crystals; m.p. 242–245° C.; $^1$H-NMR (DMSO-d$_6$): δ 0.89 (t, 3H, CH$_2$CH$_3$), 1.15 (d, 3H, CHCH$_3$), 1.50 (m, 2H, CH$_2$), 3.76 (m, 1H, CH), 7.19 (br.s, 1H, NH), 7.29 (m, 2H, ArH), 7.68 (d, 1H,ArH), 10.35 (br.s, 1H, NH); MS: m/e 287/289 (M+); (C$_{11}$H$_{14}$Cl$_1$O$_3$S$_1$) calc. C45.91 H, 4.90; N, 14.60; found C, 46.42; H, 5.08; N, 14.65.

Example 43

6-Chloro-3-cyclohexylmethylamino-4H-1,2,4-benzothiadiazine 1,1-dioxide

A mixture of 2-amino-4-chlorobenzenesulfonamide (2.1 g, 10.16 mmol) and cyclohexylmethyl isothiocyanate (6.31 g, 40.6 mmol) was heated at 150° C. for 4 h. The mixture was allowed to cool and then stirred with 25 ml of ethyl acetate for 1 h. The precipitate was isolated by filtration and recrystallised from ethanol to give 867 mg (26%) of the title compound; m.p. 317–323° C.; $^1$H-NMR (DMSO-d$_6$): δ 0.8–1.8 (m, 11H, cyclohexyl), 3.08 (t, 2H, CH$_2$), 7.78 (m, 3H, ArH+NH), 7.68 (d, 1H, ArH), 10.52 (br.s, 1H, NH); MS: m/e 327/329 (M+); (C$_{14}$H$_{18}$N$_3$Cl$_1$O$_2$S$_1$) calc. C, 51.29; H, 5.53; N, 12.82; found C, 51.21; H, 5.72; N, 12.81.

Example 44

6-Fluoro-3-isopropylamino-4H-1,2,4-benzothiadiazine 1,1-dioxide

A mixture of 2-amino-4-fluorobenzenesulfonamide (1.9 g, 10 mmol) and isopropyl isothiocyanate (6.4 ml, 60 mmol) was heated at 140° C. for 2.5 h. The mixture was cooled to room temperature and stirred with 50 ml of ethyl acetate for 20 min. The precipitate was isolated by filtration and washed with ethyl acetate to give 355 mg (14%) of the title compound; m.p. 266–269° C.; $^1$H-NMR (DMSO-d$_6$): δ 1.18 (d, 6H, CH(CH$_3$)$_2$), 3.91 (m, 1H, CH(CH$_3$)$_2$), 7.00–7.13 (m, 2H, ArH), 7.16 (br.s, 1H, NH), 7.73 (dd, 1H, ArH), 10.4 (br.s, 1H, NH); MS: m/e 257 (M+, 25%); (C$_{10}$H$_{12}$N$_3$F$_1$O$_2$S$_1$) calc. C, 46.68; H, 4.70; N, 16.33; found C, 46.84; H, 4.88; N, 16.13.

Example 45

3-Cyclopentylamino-6-fluoro-4H-1,2,4-benzothiadiazine 1,1-dioxide

A mixture of 2-amino-4-fluorobenzenesulfonamide (1.71 g, 9 mmol) and cyclopentyl isothiocyanate (4.6 ml, 36 mmol) was heated at 140° C. for 4 h. The mixture was cooled to room temperature and stirred with 50 ml of ethyl acetate. The precipitate was isolated by filtration and recrystallised from ethanol to give 591 mg (23%) of the title compound; m.p. 295–298° C.; $^1$H-NMR (DMSO-d$_6$): δ 1.37–2.02 (m, 8H, cyclopentyl), 4.05 (sext, 1H, CH), 6.97–715 (m, 2H, ArH), 7.32 (br.s, 1H, NH), 7.72 (dd, 1H, ArH), 10.35 (br.s, 1H, NH; MS: m/e 283 (M+, 21%); ($C_{12}H_{14}N_3F_1O_2S_1$) calc. C, 50.87; H, 4.98; N, 14.83; found C, 50.75; H, 5.12; N, 14.93.

Example 46

7-Chloro-3-isopropylamino-5-nitro-4H-1,2,4-benzothiadiazine 1,1-dioxide

The title compound was prepared from 2-amino-5-chloro-3-nitrobenzenesulfonamide and isopropyl isothiocyanate by a method analogous to the one described in Example 4; m.p. 266–267° C.; $^1$H-NMR (DMSO-d$_6$): δ 1.20 (d, 6H, CH(CH$_3$)$_2$), 3.92 (m, 1H, CH(CH$_3$)$_2$), 8.19 (d, 1H, ArH), 8.48 (d, 1H, ArH), 8.72 (br.s, 1H, NH), 10.57 (br.s, 1H, NH); MS: m/e 318/320 (M+); ($C_{10}H_{11}N_4Cl_1O_4S_1$) calc. C, 37.68; H, 3.48; N, 17.58, found C, 37.82; H, 3.54; N, 17.58.

Example 47

3-tert-Butylamino-6-chloro-4H-1,2,4-benzothiadiazine 1,1-dioxide

The title compound was prepared from 2-amino-4-chlorobenzenesulfonamide and tert-butyl isothiocyanate by a method analogous to the one described in Example 4 except that the mixture was heated at 60° C. for 6 days. The intermediate N-(2-amino-4-chlorobenzenesulfonyl)-N'-tert-butylthiourea and the ring closed product were both purified by column chromatography; m.p. 291–294° C. (light petroleum/ethyl acetate); $^1$H-NMR (DMSO-d$_6$): δ 1.39 (s, 9H, C(CH$_3$)$_3$), 6.92 (br s, 1H, NH), 7.17 (d, 1H, ArH), 7.28 (dd, 1H, ArH), 7.68 (d, 1H, ArH), 10.25 (br.s, 1H, NH); MS: m/e 287/289 (M+).

Example 48

7-Iodo-3-isopropylamino-4H-1,2,4-benzothiadiazine 1,1-dioxide

The title compound was prepared from 2-amino-5-iodobenzenesulfonamide and isopropyl isothiocyanate by a method analogous to the one described in Example 4; m.p. 305–307° C. dec; $^1$H-NMR (DMSO-d$_6$): δ 1.17 (d, 6H, CH(CH$_3$)$_2$), 3.91 (m, 1H, CH(CH$_3$)$_2$), 7.02 (d, 1H, ArH), 7.15 (br., 1H, NH), 7.8–7.9 (m, 2H, ArH), 10.43 (br.s, 1H, NH); MS: m/e 365 (M+, 27%); ($C_{10}H_{12}N_3I_1O_2S_1$) calc. C, 32.89; H, 3.31; N, 11.51, found C, 32.79; H, 3.41; N, 11.27.

Example 49

6-Chloro-7-fluoro-3-isopropylamino-4H-1,2,4-benzothiadiazine 1,1-dioxide

The title compound was prepared from 2-amino-4-chloro-5-fluorobenzenesulfonamide and isopropyl isothiocyanate by a method analogous to the one described in Example 4; m.p. 282–285° C. (ethyl acetate); $^1$H-NMR (DMSO-d$_6$): δ 1.17 (d, 6H, CH(CH$_3$)$_2$), 3.92 (m, 1H, CH(CH$_3$)$_2$), 7.34 (br., 1H, NH), 7.45 (d, 1H, ArH), 7.76 (d, 1H, ArH), 10.44 (br.s, 1H, NH); MS: m/e 291/293 (M+); ($C_{10}H_{11}N_3Cl_1F_1O_2S_1$) calc. C, 41.17; H, 3.80; N, 14.40; found C, 41.3; H, 3.8; N, 14.4.

Example 50

3-Isopropylamino-6-trifluoromethyl-4H-1,2,4-benzothiadiazine 1,1-dioxide

The title compound was prepared from 2-amino-4-trifluoromethylbenzenesulfonamide and isopropyl isothiocyanate by a method analogous to the one described in Example 4; m.p. 294–297° C. (ethyl acetate); $^1$H-NMR (DMSO-d$_6$): δ 1.20 (d, 6H, CH(CH$_3$)$_2$), 3.95 (m, 1H, CH(CH$_3$)$_2$), 7.42 (br., 1H, NH), 7.56 (m, 2H, ArH), 7.99 (d, 1H, ArH), 10.55 (br.s, 1H, NH); MS: m/e 307 (M+, 33%); ($C_{11}H_{12}N_3F_3O_2S_1 \cdot H_2O$) calc. C, 40.6; H, 4.3; N, 12.9; found C, 41.0; H, 4.1; N, 13.1.

Example 51

7-Chloro-3-cyclopropylmethylamino-4H-1,2,4-benzothiadiazine 1,1-dioxide

The title compound was prepared from 2-amino-5-chlorobenzenesulfonamide and cyclopropylmethyl isothiocyanate by a method analogous to the one described in Example 4; m.p. 288–290° C. (ethyl acetate); $^1$H-NMR (DMSO-d$_6$): δ 0.20–0.54 (m, 4H, CH$_2$CH$_2$), 1.05 (m, 1H, CH), 3.10 (distorted t, 1H, NHCH$_2$), 7.22 (d, 1H, ArH), 7.31 (br., 1H, NH), 7.55–7.69 (m, 2H, ArH), 10.7 (br.s, 1H, NH); MS: m/e 285/287 (M+); ($C_{11}H_{12}N_3Cl_1O_2S_1$) calc. C, 46.24; H, 4.23; N, 14.71; found C, 46.48; H, 4.32; N, 14.72.

Example 52

3-Isopropylamino-7-methyl-4H-1,2,4-benzothiadiazine 1,1-dioxide

The title compound was prepared from 2-amino-5-methylbenzenesulfonamide and isopropyl isothiocyanate by a method analogous to the one described in Example 4; m.p. 266–268° C. (ethyl acetate); $^1$H-NMR (DMSO-d$_6$): δ 1.16 (d, 6H, CH(CH$_3$)$_2$), 3.91 (m, 1H, CH(CH$_3$)$_2$), 6.92 (br.d, 1H, NH), 7.06 (d, 1H, ArH), 7.35 (dd, 1H, ArH), 7.45 (d, 1H, ArH), 10.20 (br.s, 1H, NH); MS: m/e 253 (M+, 44%); ($C_{11}H_{15}N_3O_2S_1$) calc. C, 52.16; H, 5.97; N, 16.59; found C, 52.28; H, 6.19; N, 16.49.

Example 53

5,7-Dibromo-3-isopropylamino-4H-1,2,4-benzothiadiazine 1,1-dioxide

The title compound was prepared from 2-amino-3,5-dibromobenzenesulfonamide and isopropyl isothiocyanate by a method analogous to the one described in Example 4; m.p. 306–311° C. (ethyl acetate); $^1$H-NMR (DMSO-d$_6$): δ 1.19 (d, 6H, CH(CH$_3$)$_2$), 3.90 (m, 1H, CH(CH$_3$)$_2$), 7.82 (d, 1H, ArH), 7.92 (br.d, 1H, NH), 8.16 (d, 1H, ArH), 9.65 (br.s, 1H, NH); MS: m/e 395/397/399 (M+); ($C_{10}H_{11}N_3Br_2O_2S_1$) calc. C, 30.25; H, 2.79; N, 10.58; found C, 30.34; H, 2.77; N, 10.48.

Example 54

6-Acetyl-3-isopropylamino-4H-1,2,4-benzothiadiazine 1,1-dioxide

The title compound was prepared from 4-acetyl-2-aminobenzenesulfonamide and isopropyl isothiocyanate by a method analogous to the one described in Example 4; m.p. 305–308° C. (ethyl acetate); $^1$H-NMR (DMSO-d$_6$): δ 1.19 (d, 6H, CH(CH$_3$)$_2$), 3.95 (m, 1H, CH(CH$_3$)$_2$), 7.25 (br., 1H, NH), 7.70–7.85 (m, 3H, ArH), 10.5 (br.s, 1H, NH); MS: m/e 281 (M+; 39%); (C$_{12}$H$_{15}$N$_3$O$_3$S$_1$) calc. C, 51.23; H, 5.37; N, 14.94, found C, 51.15; H, 5.50; N, 14.69.

Example 55

3-Allylamino-6-chloro-4H-1,2,4-benzothiadiazine 1,1-dioxide

The title compound was prepared from 2-amino-4-chlorobenzenesulfonamide and allyl isothiocyanate by a method analogous to the one described in Example 4; m.p. 284–286° C. (ethyl acetate); $^1$H-NMR (DMSO-d$_6$): δ 3.88 (distorted t, 2H, NHCH$_2$), 5.1–5.3 (m, 2H, =CH$_2$), 5.78–6.0 (m, 1H, =CH), 7.22–7.35 (m, 2H, ArH), 7.50 (br.t, 1H, NH), 7.69 (d, 1H, ArH), 10.73 (br.s, 1H, NH); MS: m/e 271/273 (M+); (C$_{10}$H$_{10}$N$_3$Cl$_1$O$_2$S$_1$) calc. C, 44.20; H, 3.71 N, 15.46; found C, 44.10; H, 3.79; N, 15.32.

Example 56

3-Isopropylamino-7-nitro-4H-1,2,4-benzothiadiazine 1,1-dioxide
a) 2-Chloro-5-nitrobenzenesulfonamide
Glacial acetic acid (160 mL) was saturated with gaseous sulfur dioxide and then supplemented with an aqueous solution of cupric chloride (7 g/20 mL). A solution of 2-chloro-5-nitroaniline (10 g) in glacial acetic acid (160 mL) and 12N HCl (40 mL) was cooled to −5° C. A solution of sodium nitrite (4 g) in water (20 mL) was then added dropwise under stirring to the cold solution of 2-chloro-5-nitroaniline. The diazonium salt formed was added under stirring to the cold solution of sulfur dioxide in acetic acid previously prepared. After 10 min., the mixture was poured on ice (200 g). The resulting precipitate was collected by filtration, washed with water and suspended in a 10% aqueous solution of ammonia (200 mL). After stirring at room temperature for 30 min., the mixture was concentrated to the half volume by evaporation under reduced pressure. The resulting suspension was adjusted to pH 1 with 12N HCl. The insoluble material was collected by filtration, washed with water and crystallized from methanol-water to give 8.8 g of the title compound; m.p. 174–176° C.
b) 2-Amino-5-nitrobenzenesulfonamide
A suspension of 2-chloro-5-nitrobenzenesulfonamide (8 g) in concentrated aqueous ammonia (80 mL) was saturated with ammonia just before its introduction into a sealed vessel. The former was placed in an autoclave and heated at 120° C. for 5 h. The reaction mixture was then concentrated to the half volume by evaporation under reduced pressure and the resulting precipitate was collected by filtration, washed with water and dried to give the title compound (yield: 6.1 g); m.p. 202–204° C.
c) 3-(Imidazol-1-yl)-7-nitro-4H-1,2,4-benzothiadiazine 1,1-dioxide imidazolium salt
To a hot solution of 2-amino-5-nitrobenzenesulfonamide (5 g) in dioxane (150 mL) was added thiocarbonyldiimidazole (14 g) and the reaction mixture was refluxed for 5 h. After cooling, the precipitate of the title compound was collected by filtration, washed with dioxane and dried to give the title compound (yield 5.7 g ); m.p. 246–248° C.
d) 3-Isopropylamino-7-nitro-4H-1,2,4-benzothiadiazine 1,1-dioxide
3-(Imidazol-1-yl)-7-nitro-4H-1,2,4-benzothiadiazine 1,1-dioxide imidazolium salt was treated with isopropylamine according to the general procedure Method A to give the title compound; m.p. 311–313° C.; IR (KBr): 3363, 3221, 2980, 1657, 1646,1615, 1601, 1572, 1532, 1494, 1339, 1284, 1267, 1155, 1106 cm$^{−1}$; $^1$H-NMR (DMSO-d$_6$, HMDS; d ppm): 1.10 (d, 6H, 2×CH$_3$), 3.90 (m, 1H, NH—CH), 7.35 (m, 2H, 5-H+NH—CH), 8.35 (m, 2H, 6-H+8-H), 10.90 (bs, 1H, NH).

Example 57

3-sec-Butylamino-7-nitro-4H-1,2,4-benzothiadiazine 1,1-dioxide 3-(Imidazol-1-yl)-7-nitro-4H-1,2,4-benzothiadiazine 1,1-dioxide imidazolium salt was treated with sec-butylamine according to the general procedure Method A to give the title compound; m.p. 287–288° C.

Example 58

3-(1,2-Dimethylpropyl)amino-7-nitro-4H-1,2,4-benzothiadiazine 1,1-dioxide 3-(Imidazol-1-yl)-7-nitro-4H-1,2,4-benzothiadiazine 1,1-dioxide imidazolium salt was treated with 1,2-dimethylpropylamine according to the general procedure Method B to give the title compound; m.p. 308–311° C.; IR (KBr): 3294, 3199, 3101, 2965, 1636, 1600, 1566, 1538, 1497, 1485, 1349, 1252, 1166, 1153, 1107 cm$^{−1}$.

Example 59

3-(Cyclopropylmethyl)amino-7-nitro-4H-1,2,4-benzothiadiazine 1,1-dioxide 3-(Imidazol-1-yl)-7-nitro-4H-1,2,4-benzothiadiazine 1,1-dioxide imidazolium salt was treated with cyclopropylmethylamine according to the general procedure Method D to give the title compound; m.p.: 276–278° C.; IR (KBr): 3290, 3193, 3104, 2994, 1635, 1603,1564, 1539, 1499, 1486, 1347, 1276, 1251,1153, 1111 cm$^{−1}$.

Example 60

7-Nitro-3-propylamino-4H-1,2,4-benzothiadiazine 1,1-dioxide 3-(Imidazol-1-yl)-7-nitro-4H-1,2,4-benzothiadiazine 1,1-dioxide imidazolium salt was treated with propylamine according to the general procedure Method A to give the title compound; m.p. 268–270° C.

Example 61

3-Cyclobutylamino-7-nitro-4H-1,2,4-benzothiadiazine 1,1-dioxide 3-(Imidazol-1-yl)-7-nitro-4H-1,2,4-benzothiadiazine 1,1-dioxide imidazolium salt was treated with cyclobutylamine according to the general procedure Method D to give the title compound; m.p. 298–301° C.

Example 62

7-Amino-3-isopropylamino-4H-1,2,4-benzothiadiazine 1,1-dioxide

A solution of 3-isopropylamino-7-nitro-4H-1,2,4-benzothiadiazine 1,1-dioxide (0.6 g) in hot methanol (25 mL) was supplemented with 10% Pd/C (0.06 g) and submitted to hydrogen under pressure (4 bars) for 1 h at 40° C.

The insoluble material was removed by filtration and the filtrate was concentrated to dryness by evaporation under reduced pressure. The residue of the crude title compound was recrystallized from methanol-water (yield: 0.45 g); m.p.: 278–283° C.; IR (KBr): 3455, 3363, 3216, 2972, 1618, 1575, 1510, 1298, 1255, 1174, 1146, 1113 cm$^{-1}$; $^1$H-NMR (DMSO-d$_6$, HMDS; d ppm): 1.10 (d, 6H, 2×CH$_3$), 3.85 (m, 1H, NH—CH), 5.15 (bs, 2H, NH$_2$), 6.50–6.95 (bm, 4H, 5-H+6-H+8-H+NH—CH), 9.75 (bs, 1H, NH).

Example 63

7-Acetylamino-3-isopropylamino-4H-1,2,4-benzothiadiazine 1,1-dioxide

A mixture of 7-amino-3-isopropylamino-4H-1,2,4-benzothiadiazine 1,1-dioxide (0.18 g) and acetic anhydride (0.6 mL) in dioxane (2 mL) was stirred for 1 h at room temperature. The medium was then mixed with water (5 mL) and stirred for 1 h. The solvents were removed by distillation under reduced pressure and the residue of the crude title compound was recrystallized from methanol-water to give the title compound (yield: 0.16 g); m.p. 260–262° C.; IR (KBr): 3353, 3316, 3240, 3101, 3069, 2974, 1672, 1624, 1608, 1581, 1546, 1497, 1467, 1391, 1279, 1159, 1142, 1123, 1104 cm$^{-1}$; $^1$H-NMR (DMSO-d$_6$, HMDS; d ppm): 1.10 (d, 6H, 2×CH$_3$), 2.00 (s, 3H, COCH$_3$), 3.90 (m, 1H, NH—CH), 6.85 (bd, 1H, NH—CH), 7.05 (d, 1H, 5-H), 7.60 (bd, 1H, 6-H), 8.00 (bs, 1H, 8-H), 10.00 (bs, 1H, CONH), 10.10 (bs, 1H, NH).

Example 64

6,7-Dichloro-3-hexylamino-4H-1,2,4-benzothiadiazine 1,1-dioxide a) 6,7-Dichloro-3-(imidazol-1-yl)-4H-1,2,4-benzothiadiazine 1,1-dioxide monohydrate A mixture of 2-amino-4,5-dichlorobenzenesulfonamide (10 g) and thiocarbonyldiimidazole (22 g) in dioxane (160 mL) was refluxed for 2–3 h. The solvent was removed by distillation under reduced pressure and the residue was dispersed in water (100 mL). The addition of an aqueous solution of NaOH (16 g/160 mL) gave a solution which, after cooling, abundantly precipitated the crystalline sodium salt of the title compound. The salt was collected by filtration and dissolved in a 1:2 mixture of methanol and water (300 mL), treated with charcoal, filtered, and the filtrate was adjusted to pH 2 with 12N HCl. The precipitate was collected by filtration, washed with water and dried (yield: 11.3 g); m.p.: 312–315° C.

b) 6,7-Dichloro-3-hexylamino-4H-1,2,4-benzothiadiazine 1,1-dioxide 6,7-Dichloro-3-(imidazol-1-yl)-4H-1,2,4-benzothiadiazine 1,1-dioxide monohydrate was treated with hexylamine according to the general procedure Method B to give the title compound; m.p. 282–286° C.; IR (KBr): 3332, 3173, 3074, 2956, 2930, 2854, 1637, 1580, 1562, 1464, 1241, 1168, 1143, 1132 cm$^{-1}$.

Example 65

3-Cyclobutylamino-6,7-dichloro-4H-1,2,4-benzothiadiazine 1,1-dioxide 6,7-Dichloro-3-(imidazol-1-yl)-4H-1,2,4-benzothiadiazine 1,1-dioxide monohydrate was treated with cyclobutylamine according to the general procedure Method D to give the title compound; m.p. 320–326° C.; IR (KBr): 3290, 3163, 3068, 2979, 2952, 1631, 1580, 1556, 1460, 1331, 1251, 1166, 1152, 1137, 1128 cm$^{-1}$.

In the following, Example 66 to 122, the 3-alkylamino-1,2,4-benzothiadiazine 1,1-dioxides were prepared from the appropriate 3-methylsulfanyl-1,2,4-benzothiadiazine 1,1-dioxides and the appropriate alkylamines according to the general procedure described above. For each compound the applied method and data for the compound are given.

Example 66

7-Chloro-3-(cyclohexylmethyl)amino-4H-1,2,4-benzothiadiazine 1,1-dioxide

Method C; m.p. 277–279° C.

Example 67

7-Chloro-3-(R)-(1-cyclohexylethyl)amino-4H-1,2,4-benzothiadiazine 1,1-dioxide

Method C; m.p. 177–182° C.; IR (KBr): 3300, 3187, 3085, 2927, 2853, 1631, 1581, 1483, 1251, 1162, 1105 cm$^{-1}$.

Example 68

7-Chloro-3-(S)-(1-cyclohexylethyl)amino-4H-1,2,4-benzothiadiazine 1,1-dioxide

Method C; m.p. 177–182° C.; IR (KBr): 3300, 3185, 3084, 2927, 2853, 1632, 1578, 1483, 1243, 1162, 1105 cm$^{-1}$.

Example 69

7-Chloro-3-(R)-(1-phenylethyl)amino-4H-1,2,4-benzothiadiazine 1,1-dioxide

Method C; m.p. 178–181° C.; IR (KBr): 3299, 3183, 3085, 2977, 1631, 1568, 1482, 1251, 1163, 1105 cm$^{-1}$.

Example 70

7-Chloro-3-(S)-(1-phenylethyl)amino-4H-1,2,4-benzothiadiazine 1,1-dioxide

Method C; m.p. 178–181° C.; IR (KBr): 3299, 3186, 3086, 2977, 1631, 1568, 1482, 1251, 1163, 1105 cm$^{-1}$.

Example 71

7-Chloro-3-cyclobutylamino-4H-1,2,4-benzothiadiazine 1,1-dioxide

Method D; m.p.: 275–278° C.; IR (KBr): 3284, 3180, 3087, 2983, 1633, 1575, 1494, 1479, 1238, 1155, 1125, 1102 cm$^{-1}$; NMR (DMSO-d$_6$, HMDS; d ppm): 1.20–2.30 (m, 6H, (CH$_2$)$_3$), 4.15 (m, 1H, NH—CH), 7.15 (d, 1H, 5-H), 7.50 (m, 2H, 6-H+NH—CH), 7.60 (s, 1H, 8-H), 10.25 (bs, 1H, NH).

Example 72

7-Chloro-3-(2,2,2-trifluoroethyl)amino-4H-1,2,4-benzothiadiazine 1,1-dioxide

Method A; m.p.: 302–304° C.; IR (KBr): 3283, 3186, 3120, 3087, 1627, 1582, 1483, 1265, 1240, 1181, 1161, 1136, 1107 cm$^{-1}$.

Example 73

3-Allylamino-7-chloro-4H-1,2,4-benzothiadiazine 1,1-dioxide

Method A; m.p.: 220–222° C.; IR (KBr): 3310, 3185, 3089, 2988, 1651, 1630, 1584, 1483, 1239, 1164, 1138, 1105 cm$^{-1}$.

Example 74

7-Chloro-3-(2-methoxy-1-methylethyl)amino-4H-1,2,4-benzothiadiazine 1,1-dioxide

Method B; m.p.: 150–153° C.; IR (KBr): 3294, 3186, 3118, 3084, 2983, 2932, 2880, 1631, 1582, 1480, 1250, 1162, 1105 cm$^{-1}$.

Example 75

7-Chloro-3-(1-ethylpropyl)amino-4H-1,2,4-benzothiadiazine 1,1-dioxide
Method B; m.p.: 233–236° C.; IR (KBr): 3290, 3191, 3119, 3087, 2968, 2934, 2879, 2859, 1627, 1582, 1482, 1242, 1158, 1146, 1121, 1102 cm$^{-1}$; NMR (DMSO-$d_6$, HMDS; d ppm): 0.75 (t, 6H, 2×CH$_3$), 1.40 (quint., 4H, 2×CH$_2$), 3.55 (m, 1H, NH—CH), 6.95 (b, 1H, NH—CH), 7.10 (d, 1H, 5-H), 7.50 (d, 1H, 6-H), 7.55 (s, 1H, 8-H), 10.30 (bs, 1H, NH).

Example 76

7-Chloro-3-(2-hydroxypropyl)amino-4H-1,2,4-benzothiadiazine 1,1-dioxide
Method B; m.p.: 248–250° C.; IR (KBr): 3365, 3174, 3068, 2968, 1636, 1587, 1566, 1481, 1274, 1175, 1149 cm$^{-1}$.

Example 77

7-Chloro-3-(2-hydroxy-1-methylethyl)amino-4H-1,2,4-benzothiadiazine 1,1-dioxide
Method B; m.p.: 216–217° C.; IR (KBr): 3428, 3286, 3102, 1626, 1582, 1483, 1272, 1163, 1122, 1105 cm$^{-1}$; NMR (DMSO-$d_6$, HMDS; d ppm): 1.05 (d, 3H, CH$_3$), 3.30 (bd, 2H, CH$_2$), 3.80 (m, 1H, NH—CH), 4.85 (b, 1H, OH), 6.90 (bd, 1H, NH—CH), 7.10 (d, 1H, 5-H), 7.50 (d, 1H, 6-H), 7.55 (s, 1H, 8-H), 10.50 (bs, 1H, NH).

Example 78

7-Chloro-3-(2,2-diethoxyethyl)amino-4H-1,2,4-benzothiadiazine 1,1-dioxide
Method B; m.p.: 219–220° C.; IR (KBr): 3367, 3194, 3092, 2978, 1627, 1611, 1585, 1570, 1486, 1251, 1169, 1135, 1105 cm$^{-1}$; NMR (DMSO-$d_6$, HMDS; d ppm): 1.05 (t, 6H, 2×CH$_3$), 3.25 (bd, 2H, NH—CH$_2$—CH), 3.55 (q, 4H, 2×CH$_2$), 4.55 (t, 1H, NH—CH$_2$—CH), 7.00 (b, 1H, NH—CH$_2$—CH), 7.10 (d, 1H, 5-H), 7.55 (d, 1H, 6-H), 7.60 (s, 1H, 8-H), 10.65 (b, 1H, NH).

Example 79

7-Chloro-3-hexylamino-4H-1,2,4-benzothiadiazine 1,1-dioxide
Method B; m.p.: 218–220° C.

Example 80

3-(2-Butyl)amino-7-iodo-4H-1,2,4-benzothiadiazine 1,1-dioxide
Method A; m.p.: 253–254° C.; IR (KBr): 3318, 2969, 1618, 1573, 1476, 1274, 1247, 1149, 1114 cm$^{-1}$.

Example 81

7-Iodo-3-(1,2-dimethylpropyl)amino-4H-1,2,4-benzothiadiazine 1,1-dioxide
Method B; m.p.: 267–270° C.; IR (KBr): 3317, 2961, 1616, 1573, 1475, 1276, 1248, 1156, 1115 cm$^{-1}$.

Example 82

7-Iodo-3-(1,2,2-trimethylpropyl)amino-4H-1,2,4-benzothiadiazine 1,1-dioxide
Method B; m.p.: 309–310° C.; IR (KBr): 3336, 2961, 1620, 1573, 1559, 1475, 1277, 1253, 1148, 1114 cm$^{-1}$.

Example 83

3-(Cyclohexylmethyl)amino-7-iodo-4H-1,2,4-benzothiadiazine 1,1-dioxide
Method C; m.p.: 285–287° C.; IR (KBr): 3312, 2922, 2850, 1614, 1574, 1563, 1474, 1280, 1254, 1148, 1117 cm$^{-1}$.

Example 84

3-(R)-(1-Cyclohexylethyl)amino-7-iodo-4H-1,2,4-benzothiadiazine 1,1-dioxide
Method C; m.p.: 281–284° C.; IR (KBr): 3361, 3288, 3200, 2921, 2849, 1629, 1600, 1573, 1475, 1279, 1256, 1162, 1122 cm$^{-1}$.

Example 85

3-(S)-(1-Cyclohexylethyl)amino-7-iodo-4H-1,2,4-benzothiadiazine 1,1-dioxide
Method C; m.p.: 288–290° C.; IR (KBr): 3361, 3289, 3201, 2922, 2848, 1628, 1600, 1573, 1475, 1279, 1256, 1161, 1123 cm$^{-1}$.

Example 86

3-Benzylamino-7-iodo-4H-1,2,4-benzothiadiazine 1,1-dioxide
Method C; m.p.: 254–257° C.; IR (KBr): 3289, 3183, 3087, 1626, 1575, 1477, 1268, 1260, 1235, 1152, 1127 cm$^{-1}$.

Example 87

7-Iodo-3-(R)-(1-phenylethyl)amino-4H-1,2,4-benzothiadiazine 1,1-dioxide
Method C; m.p.: 234–236° C.; IR (KBr): 3360, 3281, 3191, 3077, 1627, 1600, 1567, 1473, 1281, 1255, 1162, 1132 cm$^{-1}$.

Example 88

7-Iodo-3-(S)-(1-phenylethyl)amino-4H-1,2,4-benzothiadiazine 1,1-dioxide
Method C; m.p.: 236–239° C.; IR (KBr): 3360, 3281, 3191, 3076, 1626, 1600, 1567, 1473, 1280, 1255, 1162, 1132 cm.

Example 89

3-(3-Pentyl)amino-7-iodo-4H-1,2,4-benzothiadiazine 1,1-dioxide
Method B; m.p.: 210–220° C.; IR (KBr): 3314, 2966, 2938, 2876, 1617, 1574, 1475, 1277, 1250, 1151, 1118 cm$^{-1}$; NMR (DMSO-$d_6$, HMDS; d ppm): 0.80 (t, 6H, 2×CH$_3$), 1.40 (quint., 4H, 2×CH$_2$), 3.60 (m, 1H, NH—CH), 6.95 (bm, 2H, 5-H+NH—CH), 7.75 (d, 1H, 6-H), 7.85 (s, 1H, 8-H), 10.25 (bs, 1H, NH).

Example 90

7-Bromo-3-sec-butylamino-4H-1,2,4-benzothiadiazine 1,1-dioxide
Method A; m.p.: 224–226° C.; IR (KBr): 3320, 3105, 2971, 2933, 2879, 1622, 1579, 1480, 1277, 1253, 1158, 1150, 1115 cm$^{-1}$.

Example 91

7-Bromo-3-(1,2-dimethylpropyl)amino-4H-1,2,4-benzothiadiazine 1,1-dioxide
Method B; m.p.: 254–256° C.; IR (KBr): 3319, 2963, 2876, 1618, 1578, 1562, 1478, 1282, 1252, 1160, 1151, 1116, 1101 cm$^{-1}$.

Example 92

7-Bromo-3-cyclopropylamino-4H-1,2,4-benzothiadiazine 1,1-dioxide
Method A; m.p.: 248–253° C.; IR (KBr): 3274, 3198, 3140, 1621, 1588, 1528, 1483, 1445, 1342, 1251, 1158, 1147, 1101 cm$^{-1}$.

Example 93

7-Bromo-3-methylamino-4H-1,2,4-benzothiadiazine 1,1-dioxide monohydrate

Method A (using a 40% w/v solution of methylamine in water)
m.p.: 305–307° C.

Example 94

7-Bromo-3-ethylamino-4H-1,2,4-benzothiadiazine 1,1-dioxide

Method A (using a 70% w/v solution of ethylamine in water)
m.p.: 267–268° C.; IR (KBr): 3305, 3189, 3123, 2972, 1630, 1583, 1478, 1249, 1159, 1122 cm$^{-1}$.

Example 95

7-Bromo-3-cyclobutylamino-4H-1,2,4-benzothiadiazine 1,1-dioxide

Method D
m.p.: 279–281° C.; IR (KBr): 3288, 3175, 3081, 2984, 1631, 1580, 1563, 1480, 1258, 1242, 1153, 1123 cm-$^1$.

Example 96

7-Bromo-3-(2,2,2-trifluoroethyl)amino-4H-1,2,4-benzothiadiazine 1,1-dioxide

Method A
m.p.: 298–301° C.

Example 97

7-Bromo-3-propylamino-4H-1,2,4-benzothiadiazine 1,1-dioxide

Method A
m.p.: 234–235° C.

Example 98

7-Fluoro-3-isopropylamino-4H-1,2,4-benzothiadiazine 1,1-dioxide

Method A
m.p.: 242–244° C.; IR (KBr): 3304, 3177, 3084, 2986, 1639, 1619, 1594, 1568, 1509, 1493, 1267, 1258, 1242, 1178, 1148, 1119, 1108 cm$^{-1}$; NMR (DMSO-d$_6$, HMDS; d ppm): 1.10 (d, 6H, 2×CH$_3$), 3.90 (m, 1H, NH—CH), 7.00 (bd, 1H, NH—CH), 7.10–7.50 (m, 3H, 5-H+6-H+8-H), 10.25 (bs, 1H, NH).

Example 99

3-(2-Butyl)amino-7-fluoro-4H-1,2,4-benzothiadiazine 1,1-dioxide monohydrate

Method A
m.p.: 203–205° C.; IR (KBr): 3545, 3492, 3348, 3080, 2974, 1651, 1636, 1618, 1595, 1568, 1498, 1267, 1180, 1159, 1115 cm$^{-1}$.

Example 100

7-Fluoro-3-(1,2-dimethylpropyl)amino-4H-1,2,4-benzothiadiazine 1,1-dioxide

Method B
m.p.: 193–198° C.; IR (KBr): 3298, 3189, 3089, 2968, 1636, 1616, 1593, 1572, 1504, 1494, 1258, 1168, 1147, 1110 cm$^{-1}$.

Example 101

3-Ethylamino-7-fluoro-4H-1,2,4-benzothiadiazine 1,1-dioxide

Method A (using a 70% w/v aqueous solution of ethylamine)
m.p.: 235–237° C.; IR (KBr): 3289, 3194, 3127, 3086, 2987, 2891, 1636, 1620, 1593, 1579, 1505, 1491, 1260, 1240, 1159, 1145, 1112 cm$^{-1}$.

Example 102

7-Fluoro-3-propylamino-4H-1,2,4-benzothiadiazine 1,1-dioxide

Method A
m.p.: 199–202° C.

Example 103

3-Cyclopropylamino-7-fluoro-4H-1,2,4-benzothiadiazine 1,1-dioxide

Method A
m.p.: 242–245° C.

Example 104

3-Cyclobutylamino-7-fluoro-4H-1,2,4-benzothiadiazine 1,1-dioxide

Method D
m.p.: 252–253° C.; IR (KBr): 3303, 3176, 3085, 2983, 1640, 1619, 1595, 1566, 1508, 1493, 1260, 1245, 1169, 1151, 1138, 1117 cm$^{-1}$.

Example 105

3-Cyclopentylamino-7-fluoro-4H-1,2,4-benzothiadiazine 1,1-dioxide

Method B
m.p.: 237–239° C.; IR (KBr): 3299, 3176, 3084, 3008, 2982, 2874, 1640, 1619, 1593, 1569, 1509, 1493, 1266, 1258, 1241, 1160, 1137, 1112 cm$^{-1}$.

Example 106

3-(Cyclopropylmethyl)amino-7-fluoro-4H-1,2,4-benzothiadiazine 1,1-dioxide

Method D
m.p.: 221–222° C.; IR (KBr): 3295, 3187, 3086, 3008, 2884, 1641, 1620, 1592, 1508, 1496, 1270, 1256, 1240, 1155, 1137, 1115 cm$^{-1}$.

Example 107

3-Allylamino-7-fluoro-4H-1,2,4-benzothiadiazine 1,1-dioxide

Method A
m.p.: 209–210° C.; IR (KBr): 3353, 3312, 3187, 3087, 2989, (1636), 1615, 1595, 1569, 1493, 1259, 1164, 1141, 1119 cm$^{-1}$.

Example 108

7-Fluoro-3-(3-methoxy-2-propyl)amino-4H-1,2,4-benzothiadiazine 1,1-dioxide (or 7-Fluoro-3-(2-methoxy-1-methylethyl)amino-4H-1,2,4-benzothiadiazine 1,1-dioxide Method B
m.p.: 148–149° C.; IR (KBr): 3309, 3201, 3137, 3099, 2986, 2934, 2900, 1636, 1618, 1594, 1580, 1507, 1494, 1260, 1149, 1111 cm$^{-1}$.

Example 109

7-Fluoro-3-methylamino-4H-1,2,4-benzothiadiazine 1,1-dioxide monohydrate

Method A (using a 40% w/v aqueous solution of methylamine)
m.p.: 275–277° C.

Example 110

3-(2,2-Diethoxyethyl)amino-7-fluoro-4H-1,2,4-benzothiadiazine 1,1-dioxide

Method B
m.p.: 202–203° C.

Example 111

7-Fluoro-3-(2,2,2-trifluoroethyl)amino-4H-1,2,4-benzothiadiazine 1,1-dioxide

Method A
m.p.: 269–271° C.

Example 112

3-Cyclobutylamino-7-methyl-4H-1,2,4-benzothiadiazine 1,1-dioxide

Method D
m.p.: 289–290° C.; IR (KBr): 3285, 3179, 3088, 2986, 2947, 1631, 1587, 1568, 1500, 1269, 1239, 1149, 1122 cm$^{-1}$.

Example 113

3-Isopropylamino-7-methoxy-4H-1,2,4-benzothiadiazine 1,1-dioxide

Method A
m.p.: 227–233° C.; IR (KBr): 3285, 3128, 2969, 2925, 1628, 1609, 1580, 1505, 1273, 1254, 1147, 1121, 1109 cm$^{-1}$; NMR (DMSO-d$_6$, HMDS; d ppm): 1.10 (d, 6H, 2×CH$_3$), 3.70 (s, 3H, OCH$_3$), 3.90 (m, 1H, NH—CH), 6.85 (bd, 1H, NH—CH), 7.10 (s, 3H, 5-H+6-H+8-H), 10.05 (bs, 1H, NH).

Example 114

7-Methoxy-3-propylamino-4H-1,2,4-benzothiadiazine 1,1-dioxide monohydrate

Method A
m.p.: 194–199° C.

Example 115

6-Chloro-3-cyclobutylamino-4H-1,2,4-benzothiadiazine 1,1-dioxide

Method D
m.p. 306–307° C.; IR (KBr): 3333, 3285, 3181, 3079, 2993, 2951, 1631, 1583, 1549, 1470, 1245, 1167, 1149, 1124 cm$^{-1}$.

Example 116

6-Chloro-3-(2,2,2-trifluoroethyl)amino-4H-1,2,4-benzothiadiazine 1,1-dioxide

Method A
m.p.: 320–323° C.; IR (KBr): 3298, 3185, 3122, 3082, 3023, 2977, 1636, 1586, 1574, 1473, 1257, 1245, 1188, 1167, 1152, 1134 cm$^{-1}$.

Example 117

6-Chloro-3-cyclopropylmethylamino-4H-1,2,4-benzothiadiazine 1,1-dioxide

Method D
m.p. 278–280° C.; IR (KBr): 3304, 3173, 3071, 3009, 2979, 1636, 1584, 1560, 1473, 1242, 1164, 1124 cm$^{-1}$.

Example 118

5-Chloro-3-cyclobutylamino-4H-1,2,4-benzothiadiazine 1,1-dioxide

Method D
m.p. 222–224° C.

Example 119

5-Chloro-3-propylamino-4H-1,2,4-benzothiadiazine 1,1-dioxide

Method A
m.p.: 196–197° C.

Example 120

5-Chloro-3-hexylamino-4H-1,2,4-benzothiadiazine 1,1-dioxide

Method B
m.p.: 164–165° C.

Example 121

6-Chloro-3-octylamino-4H-1,2,4-benzothiadiazine 1,1-dioxide

Method C
m.p.: 231–232° C.

Example 122

6-Chloro-3-(1,5-dimethylhexyl)amino-4H-1,2,4-benzothiadiazine 1,1-dioxide

Method C
m.p.: 207–208° C.

Example 123

7-Chloro-4-methyl-3-methylsulfanyl-4H-1,2,4-benzothiadiazine 1,1-dioxide

A solution of 7-chloro-3-methylsulfanyl-4H-1,2,4-benzothiadiazine 1,1-dioxide (0.8 g) in acetonitrile (24 mL) and methanol (0.5 mL) was supplemented with potassium carbonate (0.96 g), then with methyl iodide (3 mL), and stirred at room temperature for 10 h. The solvent was removed by distillation under reduced pressure. The residue was suspended in water (40 mL) and the pH was adjusted to pH 2 with formic acid. The precipitate of the title compound was collected by filtration, washed with water and dried. The compound was used without further purification in the next step (yield: 0.53 g).

7-Chloro-3-isopropylamino-4-methyl-4H-1,2,4-benzothiadiazine 1,1-dioxide hemi-hydrate A mixture of 7-chloro-4-methyl-3-methylsulfanyl-4H-1,2,4-benzothiadiazine 1,1-dioxide (0.4 g) in isopropylamine (4 mL) was refluxed for 90 min. The amine was removed by distillation under reduced pressure, and the residue was suspended in water (20 mL). After stirring for 1 h at room temperature, the precipitate of the crude title compound was collected by filtration, washed with water and recrystallized from methanol:water (yield: 0.27 g); m.p. 176–183° C.

Example 124

3-(2-Aminoethyl)amino-7-chloro-4H-1,2,4-benzothiadiazine 1,1-dioxide monohydrate A solution of 7-chloro-3-methylsulfanyl-4H-1,2,4-benzothiadiazine 1,1-dioxide (1 g) in ethylenediamine (2.5 mL) was refluxed for 45 min. Most of the excess of amine was removed by distillation under reduced pressure and the resulting oily residue was dissolved in methanol (10 mL). Addition of diethylether (40 mL) gave rise to the precipitation of an oil which turned to a white solid after a stirring of 30 min. at 0° C. The precipitate was collected by filtration, washed with diethylether and dried. The solid was dissolved in boiling water (40 mL) and traces of insoluble material were removed by filtration. The filtrate was concentrated to the half volume by distillation under reduced pressure and placed at +4° C. for 2 h. The crystalline precipitate of the title compound was cpllected by filtration, washed with a small volume of water and dried to give the title compound (yield: 0.62 g); m.p. 200–204° C.; IR (KBr): 3498, 3372, 2932, 1637, 1560, 1481, 1264, 1163 cm$^{-1}$; $^1$H-NMR (DMSO-d$_6$, HMDS; δ ppm): 2.70 (t, 2H, NH—CH$_2$—CH$_2$—NH$_2$), 3.20 (t, 2H, NH—CH$_2$—CH$_2$—NH$_2$), 5.25 (b, 6H, 2×NH+H$_2$O+NH$_2$), 6.95 (d, 1H, 5-H), 7.30 (d, 1H, 6-H), 7.45 (s, 1H, 8-H).

Example 125

3-Isopropylamino-4H-1,2,4-benzothiadiazine-7-carboxylic acid 1,1-dioxide a) 3-Oxo-2,3-dihydro-4H-1,2,4-benzothiadiazine-7-carboxylic acid 1,1-dioxide monohydrate 7-Methyl-3-oxo-2,3-dihydro-4H-1,2,4-benzothiadiazine 1,1-dioxide (20 g) was suspended in hot water (2000 mL) and supplemented dropwise with a 10% aqueous solution of NaOH until complete dissolution. Potassium permanganate (60 g) was added portionwise and the reaction mixture was stirred for 3 h at 70° C. After cooling, the insoluble material was removed by filtration and the purple filtrate was treated with sodium hydrogen sulfite until complete discolouration of the excess of permanganate. The solution was treated with charcoal, filtered, and the filtrate was adjusted to pH 0 with 12N HCl. The resulting suspension was placed at +4° C. during 2 h and the crystalline precipitate was collected by filtration, washed with water and dried (yield: 14.5 g); m.p.: 305–308° C.

b) 4-Amino-3-sulfamoylbenzoic acid

A suspension of 3-oxo-2,3-dihydro-4H-1,2,4-benzothiadiazine-7-carboxylic acid 1,1-dioxide monohydrate (10 g) in a mixture of concentrated sulfuric acid (150 mL) and water (150 mL) was refluxed until complete dissolution of the starting material (1–2 h). The resulting solution was placed on an ice bath and supplemented dropwise with a 20% aqueous solution of NaOH under stirring and cooling until pH 1–2. The precipitate was collected by filtration, washed with water and dried (yield: 6.6 g); m.p.: 214–219° C.

c) 3-(Imidazol-1-yl)-4H-1,2,4-benzothiadiazine-7-carboxylic acid 1,1-dioxide

4-Amino-3-sulfamoylbenzoic acid (6 g) and thiocarbonyldiimidazole (23.2 g) in dioxane (60 mL) was refluxed for 2 h. The solvent was removed by distillation under reduced pressure. The residue was dispersed in water (200 mL) and supplemented with a 10% aqueous solution of NaOH (40 mL). After stirring for 30 min. at room temperature, the solution was treated with charcoal, filtered, and the filtrate was adjusted to pH 2 with 12N HCl. The resulting precipitate was collected by filtration, washed with water and dried to give the title compound (yield: 4.5 g); m.p. >300° C.

d) 3-Isopropylamino-4H-1,2,4-benzothiadiazine-7-carboxylic acid 1,1-dioxide 3-(Imidazol-1-yl)-4H-1,2,4-benzothiadiazine-7-carboxylic acid 1,1-dioxide was treated with isopropylamine according to the general procedure Method A to give the title compound; m.p. >310° C.

Example 126

3-sec-Butylamino-4H-1,2,4-benzothiadiazine-7-carboxylic acid 1,1-dioxide 3-(Imidazol-1-yl)-4H-1,2,4-benzothiadiazine-7-carboxylic acid 1,1-dioxide was treated with sec-butylamine according to the general procedure Method A to give the title compound; m.p. >310° C.

Example 127

3-Propylamino-4H-1,2,4-benzothiadiazine-7-carboxylic acid 1,1-dioxide 3-(Imidazol-1-yl)-4H-1,2,4-benzothiadiazine-7-carboxylic acid 1,1-dioxide was treated with propylamine according to the general procedure Method A to give the title compound; m.p. >310° C.

Example 128

3-Isopropylamino-7-trifluoromethyl-4H-1,2,4-benzothiadiazine 1,1-dioxide a) 2-Amino-5-trifluoromethylbenzenesulfonamide A solution of 2-benzylamino-5-trifluoromethylbenzenesulfonamide (7.3 g) in methanol (80 mL) was supplemented with 10% Pd/C (0.73 g) and submitted to hydrogen under pressure (4 bars) during 90 min. at room temperature. The insoluble material was removed by filtration and the filtrate was concentrated to dryness. The residue was crystallized in methanol-water to give the title compound (yield: 5 g); m.p. 142–143° C.

b) 3-(Imidazol-1-yl)-7-trifluoromethyl-4H-1,2,4-benzothiadiazine 1,1-dioxide

The procedure described for 3-(imidazol-1-yl)-4H-1,2,4-benzothiadiazine-7-carboxylic acid 1,1-dioxide was used for the preparation of the title compound starting from 2-amino-5-trifluoromethylbenzenesulfonamide (4.5 g) and using a refluxing time of 4 h. The crude compound was recrystallized from methanol-diethylether (yield: 1.9 g); m.p. 211–214° C.

c) 3-Isopropylamino-7-trifluoromethyl-4H-1,2,4-benzothiadiazine 1,1-dioxide 3-(Imidazol-1-yl)-7-trifluoromethyl-4H-1,2,4-benzothiadiazine 1,1-dioxide was treated with isopropylamine according to the general procedure Method A to give the title compound; m.p. 287–289° C.

Example 129

3-sec-Butylamino-7-trifluoromethyl-4H-1,2,4-benzothiadiazine 1,1-dioxide 3-(Imidazol-1-yl)-7-trifluoromethyl-4H-1,2,4-benzothiadiazine 1,1-dioxide was treated with sec-butylamine according to the general procedure Method A to give the title compound; m.p. 234–236° C.

Example 130

3-Propylamino-7-trifluoromethyl-4H-1,2,4-benzothiadiazine 1,1-dioxide 3-(Imidazol-1-yl)-7-trifluoromethyl-4H-1,2,4-benzothiadiazine 1,1-dioxide was treated with propylamine according to the general procedure Method A to give the title compound; m.p. 241–243° C.

Example 131

3-Cyclopropylmethylamino-7-trifluoromethyl-4H-1,2,4-benzothiadiazine 1,1-dioxide 3-(Imidazol-1-yl)-7-trifluoromethyl-4H-1,2,4-benzothiadiazine 1,1-dioxide was treated with cyclopropylmethylamine according to the general procedure Method D to give the title compound; m.p. 266–268° C.

Example 132

7-Fluoro-3,6-di(isopropylamino)-4H-1,2,4-benzothiadiazine 1,1-dioxide a) 2-Amino-4,5-difluorobenzenesulfonamide 3,4-Difluoroaniline (20 g) in chlorosulfonic acid (60 mL) was heated for 1 h at 140° C. After cooling at 70° C., the reaction mixture was supplemented with thionyl chloride (30 mL) and refluxed for 2 h. After cooling, the mixture was poored on ice water (200 g) and extracted three times with diethyl ether (3×100 mL). The combined organic layers were dried over MgSO$_4$, filtered and concentrated to dryness under reduced pressure. The oily residue was dissolved in dioxane (100 mL) and added under stirring to a 10% w/v aqueous solution of ammonia (300 mL). After 1 h, the resulting solution was treated with charcoal, filtered and concentrated to a volume of 100 mL, then adjusted to pH 3. After standing overnight at +4° C., the precipitate was collected by filtration and washed with the minimum of water (first part). The filtrate was extracted three times with ethyl acetate (3×100 mL). The combined organic layers were dried over MgSO$_4$, filtered, and the filtrate was concentrated to dryness. The residue was suspended in a small volume of water, and the insoluble material was collected by filtration, washed with a minimum of water and dried (second part) (total yield of crude compound: 5.5 g); m.p. 137–142° C. (methanol-diethylether).

b) 6,7-Difluoro-3-(imidazol-1-yl)-4H-1,2,4-benzothiadiazine 1,1-dioxide

The procedure described for 3-(imidazol-1-yl)-4H-1,2,4-benzothiadiazine-7-carboxylic acid 1,1-dioxide was used for the preparation of the title compound starting from 2-amino-4,5-difluorobenzenesulfonamide (5 g) and using a refluxing time of 4 h. The crude compound was recrystallized from acetone-diethylether (yield: 2.6 g); m.p. 264–266° C.

c) 7-Fluoro-3,6-di(isopropylamino)-4H-1,2,4-benzothiadiazine 1,1-dioxide 6,7-Difluoro-3-(imidazol-1-yl)-4H-1,2,4-benzothiadiazine 1,1-dioxide was treated with isopropylamine according to the general procedure Method A to give the title compound; m.p. 234–237° C.

Example 133

3-Ethylamino-6,7-difluoro-4H-1,2,4-benzothiadiazine 1,1-dioxide

Starting from 2-amino-4,5-difluorobenzenesulfonamide and ethyl isothiocyanate, and following a procedure analogous to the one described in Example 4a, N-(2-amino-4,5-difluorobenzenesulfonyl)-N'-ethylthiourea was prepared. The crude compound was used without further purification in a cyclisation step analogous to the one described in Example 4b to give the title compound; m.p. 246–252° C.

Example 134

7-Chloro-3-(pyridin-2-yl)amino-4H-1,2,4-benzothiadiazine 1,1-dioxide a) 7-Chloro-3-methylsulfinyl-4H-1,2,4-benzothiadiazine 1,1-dioxide A suspension of 7-chloro-3-methylsulfanyl-4H-1,2,4-benzothiadiazine 1,1-dioxide (0.5 g) in an aqueous solution of sodium hydrogen carbonate (0.22 g/25 mL) was supplemented dropwise with 2M NaOH until complete dissolution. Liquid bromine (0.1 mL) was added under stirring at room temperature. After 10 min., the resulting suspension was adjusted to pH 2–3 with 6N HCl and the insoluble material was collected by filtration and washed with water. The white precipitate was suspended in methanol (20 mL), stirred for 1 h and then collected by filtration, washed with methanol and dried (yield: 0.45 g); m.p. 260–261° C.

b) 7-Chloro-3-(pyrid-2-yl)amino-4H-1,2,4-benzothiadiazine 1,1-dioxide

7-Chloro-3-methylsulfinyl-4H-1,2,4-benzothiadiazine 1,1-dioxide (0.25 g) and 2-aminopyridine (0.25 g) in 3-chlorotoluene (5 mL) was heated at 150° C. for 1 h. After cooling, the white precipitate was collected by filtration and washed with diethylether. The insoluble material was dissolved in 1M NaOH (20 mL), treated with charcoal, filtered, and the filtrate was adjusted to pH 3 with 6N HCl. The precipitate was collected by filtration, washed with water, dissolved in hot DMF (15 mL), mixed with an equal volume of distilled water and cooled. The white precipitate was collected by filtration, washed with water and dried (yield: 0.12 g); m.p. >310° C.

Example 135

7-Chloro-3-(2-formylaminoethyl)amino-4H-1,2,4-benzothiadiazine 1,1-dioxide

A mixture of formic acid (1 mL) and acetic anhydride (2 mL) was heated at 50° C. for 20 min. After cooling at room temperature, 3-(2-aminoethyl)amino-7-chloro-4H-1,2,4-benzothiadiazine 1,1-dioxide monohydrate (0.5 g) was added, and the reaction mixture was stirred for 2 h, then supplemented with water (20 mL) and stirred for 20 min. The precipitate was collected by filtration, washed with water and dried (yield: 0.3 g); m.p. 245–247° C.

Example 136

3-(2-Acetylaminoethyl)amino-7-chloro-4H-1,2,4-benzothiadiazine 1,1-dioxide

The same process as described in the preceding example was used for the synthesis of the title compound using 3-(2-aminoethyl)amino-7-chloro-4H-1,2,4-benzothiadiazine 1,1-dioxide monohydrate (0.5 g) and acetic anhydride (3 mL) instead of the mixture of formic acid and acetic anhydride (yield: 0.25 g); m.p. 295–297° C.

Example 137

7-Chloro-3-(1,2-dimethylpropyl)amino-2-methyl-2H-1,2,4-benzothiadiazine 1,1-dioxide To 10 ml of dry tetrahydrofuran stirred under nitrogen was added successively titanium tetrachloride (0.2 ml), anisole (0.5 ml), 1,2-dimethylpropylamine (0.8 ml), and then a slurry of 7-chloro-2,3-dihydro-2-methyl-3-oxo-4H-1,2,4-benzothiadiazine 1,1-dioxide (400 mg) in a mixture of 1,2-dimethylpropylamine (0.4 ml) and 5 ml of dry toluene. The mixture was heated at 120° C. After 1½ h an additional amount of 1,2-dimethylpropylamine (0.4 ml) was added. After 2½ h the reaction mixture was cooled to room temperature. Isopropyl alcohol (1 ml), concentrated ammonium hydroxide (1 ml) and diatomaceous earth (0.5 g) was added and stirring was continued for 15 min. The insoluble material was removed by filtration and the filter cake rinsed with two portions of 25 ml of ethyl acetate. The organic phases were combined and shaken with 25 ml of water, then with 25 ml of saturated aqueous sodium chloride, dried over sodium sulfate and the solvent was removed in vacuo. The residue was dissolved in 50 ml of ethyl acetate and extracted with 2×50 ml of 4 M hydrochloric acid. The aqueous extracts were made alkaline with concentrated ammonium hydroxide and then extracted with 2×50 ml of ethyl acetate. The organic phase was dried over sodium sulfate and the solvent removed in vacuo. The residue was purified on a silica gel column with a 7:3 mixture of n-heptane and ethyl acetate as solvent to give the title compound as white crystals; m.p. 102–105° C.

Example 138

7-Chloro-3-isopropylamino-2-methyl-2H-1,2,4-benzothiadiazine 1,1-dioxide

Triethyloxonium tetrafluoroborate (0.95 g) in 10 ml of dry dichloromethane was added under nitrogen to a stirred suspension of 7-chloro-2,3-dihydro-2-methyl-3-oxo-4H-1,2,4-benzothiadiazine 1,1-dioxide (0.5 g) in 25 ml of dichloromethane at room temperature, and stirred overnight. Then the mixture was poured into 50 ml of a stirred saturated aqueous sodium bicarbonate solution. The organic layer was dried over sodium sulfate and the solvent was removed in vacuo. The residue consisting of 0.47 g of crude 7-chloro-3-ethoxy-2-methyl-2H-1,2,4-benzothiadiazine 1,1-dioxide was processed further without purification.

A mixture of crude 7-chloro-3-ethoxy-2-methyl-2H-1,2,4-benzothiadiazine 1,1-dioxide (0.45 g) and isopropylamine (4 ml) in an ethanolic sodium ethoxide solution, prepared by dissolving 0.4 g of sodium in 10 ml of ethanol, was refluxed for 3 hours and then neutralized with 4M acetic acid. The mixture was evaporated to dryness and partitioned between 25 ml of water and 25 ml of dichloromethane. The organic layer was dried over sodium sulfate and the solvent was evaporated in vacuo. The residue was purified by chromatography on a silica gel column with a 7:3 mixture of n-heptane and ethyl acetate as solvent to give the title compound;

$^1$H-NMR (CDCl$_3$), δ (ppm): 7.7 (d, 1H), 7.47 (dd, 1H), 7.25 (d, 1H), 4.45 (br, 1H, NH), 4.38–4.18 (m, 1H, CH), 3;31 (s, 3H, CH$_3$), 1.29 (d, 6H, CH$_3$); m.p. 139–141° C.

Example 139

7-Chloro-3-(N-ethyl-N-methylamino)-4H-1,2,4-benzothiadiazine 1,1-dioxide

Starting from 3,7-dichloro-4H-1,2,4-benzothiadiazine 1,1-dioxide (753 mg; 3 mmol) and N-ethyl-N-methylamine (708 mg; 12 mmol) and with the use of same procedure as in example 21 650 mg (79%) of the title compound was prepared; m.p. >220° C.; $^1$H-NMR (DMSO-d6) ppm; 10.4 (s, 1H, NH), 7.69 (d, 1H, H-8), 7.61 (dd, 1H, H-6), 7.55 (d, 1H, H-5), 3.5 (q, 2H, CH$_2$), 3.09 (s, 3H, CH$_3$), 1.10 (t, 3H, CH$_3$); $^{13}$C-NMR (DMSO-d6) ppm; 150.21, 134.69, 131.81, 127.27, 123.98, 121.42, 119.54, 44.2, 34.69, 11.91. Analysis C$_{10}$H$_{12}$ClN$_3$O$_2$S requires C, 43.88; H, 4.42; N, 15.35; (found C, 43.52; H 4.55; N, 15.30).

Example 140

6-Chloro-3-(N-ethyl-N-methylamino)-4H-1,2,4-benzothiadiazine 1,1-dioxide

Starting from 3,6-dichloro-4H-1,2,4-benzothiadiazine 1,1-dioxide (500 mg; 1.99 mmol) and N-ethyl-N-methylamine (500 mg; 8.47 mmol) and with the use of same procedure as in example 21 200 mg (36.7%) of the title compound was prepared; m.p. >220° C.; $^1$H-NMR (DMSO-d6) ppm; 10.35 (s, 1H, NH), 7.65 (d, 1H, H-8), 7.58 (dd, 1H, H-5), 7.3 (d, 1H, H-7), 3.5 (q, 2H, CH$_2$), 3.11 (s, 3H, CH$_3$), 1.14 (t, 3H, CH$_3$). Analysis: C$_{10}$H$_{12}$ClN$_3$O$_2$S requires C, 43.88; H, 4.42; N, 15.35; (found C, 43.78; H, 4.51; N, 15.24).

Example 141

7-Chloro-3-(3-(1H-imidazol-4-yl)propyl)amino-4H-1,2,4-benzothiadiazine 1,1-dioxide A suspension of 3,7-dichloro-4H-1,2,4-benzothiadiazine 1,1-dioxide (200 mg; 0.8 mmol) and 3-(1-trityl-1H-imidazo-4(5)-yl)-propylamine (339 mg; 1.2 mmol) in ethanol (3 ml) was stirred at 90° C. in a sealed flask for 16 h. The reaction mixture was concentrated in vacu. To the residue was added 6N HCl and extracted with dichloromethane. The aqueous phase was brought to pH 10 with 10N NaOH and extracted with dichloromethane. The aqueous phase was concentrated. The residue was purified by flash chromatography using ethanol/25% aqueous ammoniumhydroxide 10:1 as eluent to give the title compound (133 mg, 49%).

$^1$H-NMR (DMSO-d$_6$), δ (ppm): 7.6 (m, 3H), 7.25 (br, 1H, NH), 6.80 (s, 1H), 3.4 (br, NH+HDO), 3.25 (q, 2H, CH$_2$), 2.48 (m, 2H+DMSO, CH$_2$), 1.78 (m, 2H, CH$_2$); MS:EI/70eV: 339, 341 ($^{35}$Cl, $^{37}$Cl) [M+].

Example 142

3-(1-Benzylpyrrolidin-3-ylamino)-7-chloro-4H-1,2,4-benzothiadiazine 1,1-dioxide A suspension of 3,7-dichloro-4H-1,2,4-benzothiadiazine 1,1-dioxide (100 mg; 0.4 mmol) 1-benzyl-3-aminopyrrolidine (0.35 ml; 2.0 mmol) was stirred at 110° C. for 72 h. The reaction mixture was concentrated in vacu and the residue was purified by flash chromatography using ethyl acetate/methanol 10:1 to give oily crystals (114 mg). These were recrystallised from ethyl acetate to give the title compound as white crystals (83 mg, 53%); m.p. 208.5–209.5° C.

$^1$H-NMR (DMSO-d$_6$), δ (ppm): 10.6 (br, 1H, NH), 7.65 (d, 1H), 7.50 (dd, 1H), 7.4 (br, 1H, NH), 7.3 (m, 5H, Ph), 7.20 (d, 1H), 4.25 (m, 1H), 3.60 (s, 2H , CH$_2$Ph), 2.7 (m, 2H), 2.5 (m, 1H+DMSO), 2.32 (m, 1H), 2.22 (m, 1H), 1.68 (m, 1H); MS:EI/70eV: 389 [M-1].

| Analysis: calc. For C$_{18}$H$_{19}$ClN$_4$O$_2$S × 0.25 H$_2$O | C 54.68 | H 4.97 | N 14.17 |
|---|---|---|---|
| found | C 54.79 | H 4.96 | N 13.95 |

What is claimed is:

1. A compound of formula I

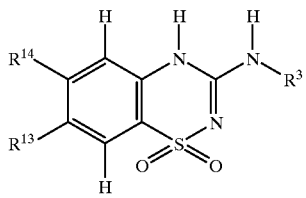

(I)

wherein
$R^3$ is $C_{3-6}$-cycloalkyl, or straight or branched $C_{1-8}$-alkyl monosubstituted with $C_{3-6}$-cycloalkyl; and
$R^{13}$ and $R^{14}$ independently are hydrogen or halogen;
or a salt thereof with a pharmaceutically acceptable acid or base, or any optical isomer or mixture of optical isomers or any tautomeric form.

2. A compound of claim 1 wherein $R^3$ is cyclobutyl.

3. A compound of claim 1 wherein $R^3$ is cyclopentyl.

4. A compound of claim 1 wherein $R^{13}$ and $R^{14}$ are chlorine.

5. A compound of claim 1 wherein $R^{13}$ is hydrogen and $R^{14}$ is chlorine.

6. A compound of claim 1 wherein $R^{13}$ is chlorine and $R^{14}$ is hydrogen.

7. A compound of claim 1 wherein $R^{13}$ is hydrogen and $R^{14}$ is fluorine.

8. A compound of claim 1 wherein $R^{13}$ is fluorine and $R^{14}$ is hydrogen.

9. A compound of claim 1 wherein $R^3$ is straight or branched $C_{1-8}$-alkyl monosubstituted with $C_{3-6}$-cycloalkyl.

10. A compound of claim 9 wherein the $C_{3-6}$-cycloalkyl is cyclopropyl.

11. A compound of claim 1 wherein $R^3$ is cyclopropylmethyl.

12. A pharmaceutical composition comprising a therapeutically effective amount of a compound of claim 1 together with a pharmaceutically acceptable carrier or diluent.

13. The pharmaceutical composition of claim 12 administered in the form of an oral dosage or parenteral dosage unit.

14. The pharmaceutical composition of claim 13 wherein the compound is administered as a dose in the range from about 0.05 to 1000 mg per day.

15. A method of treating diabetes, comprising: administering to a subject in need thereof a therapeutically effective amount of a compound of claim 1.

16. A compound which is:
3-Cyclopentylamino-6-fluoro-4H-1,2,4-benzothiadiazine 1,1-dioxide; or
3-Cyclopentylamino-7-fluoro-4H-1,2,4-benzodiathiazine 1,1-dioxide;
or a salt thereof with a pharmaceutically acceptable acid or base, or any optical isomer or mixture of optical isomers, or any tautomeric form.

17. A pharmaceutical composition comprising a therapeutically effective amount of a compound of claim 16 together with a pharmaceutically acceptable carrier or diluent.

18. The pharmaceutical composition of claim 17 administered in the form of an oral dosage or parenteral dosage unit.

19. The pharmaceutical composition of claim 18 wherein the compound is administered as a dose in the range from about 0.05 to 1000 mg per day.

20. A method of treating diabetes, comprising: administering to a subject in need thereof a therapeutically effective amount of a compound of claim 16.

21. A compound which is:
3-Cyclobutylamino-7-fluoro-4H-1,2,4-benzothiadiazine 1,1-dioxide;
7-Chloro-3-cyclobutylamino-4H-1,2,4-benzothiadiazine 1,1-dioxide
6-Chloro-3-cyclobutylamino-4H-1,2,4-benzothiadiazine 1,1-dioxide; or
6,7-Dichloro-3-cyclobutylamino-4H-1,2,4-benzothiadiazine 1,1-dioxide;
or a salt thereof with a pharmaceutically acceptable acid or base, or any optical isomer or mixture of optical isomers, or any tautomeric form.

22. A pharmaceutical composition comprising a therapeutically effective amount of a compound of claim 21 together with a pharmaceutically acceptable carrier or diluent.

23. The pharmaceutical composition of claim 22 administered in the form of an oral dosage or parenteral dosage unit.

24. The pharmaceutical composition of claim 23 wherein the compound is administered as a dose in the range from about 0.05 to 1000 mg per day.

25. A method of treating diabetes, comprising: administering to a subject in need thereof a therapeutically effective amount of a compound of claim 21.

26. A compound of claim 1 which is:
7-Chloro-3-cyclopropylmethylamino-4H-1,2,4-benzothiadiazine 1,1-dioxide; or
6-Chloro-3-cyclopropylmethylamino-4H-1,2,4-benzothiadiazine 1,1-dioxide;
or a salt thereof with a pharmaceutically acceptable acid or base, or any optical isomer or mixture of optical isomers, or any tautomeric form.

27. A pharmaceutical composition comprising a therapeutically effective amount of a compound of claim 26 together with a pharmaceutically acceptable carrier or diluent.

28. The pharmaceutical composition of claim 27 administered in the form of an oral dosage or parenteral dosage unit.

29. The pharmaceutical composition of claim 28 wherein the compound is administered as a dose in the range from about 0.05 to 1000 mg per day.

30. A method of treating diabetes, comprising: administering to a subject in need thereof a therapeutically effective amount of a compound of claim 26.

31. A compound of formula I

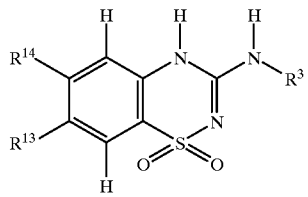

(I)

wherein
$R^3$ is straight or branched $C_{1-8}$-alkyl;
$R^{13}$ is $C_{1-6}$-alkoxy; and
$R^{14}$ is hydrogen or halogen;
or a salt thereof with a pharmaceutically acceptable acid or base, or any optical isomer or mixture of optical isomers, or any tautomeric form.

32. A compound of claim 31 wherein $R^3$ is isopropyl.

33. A compound of claim 31 wherein $R^{13}$ is methoxy.

34. A compound of claim 31 wherein $R^3$ is isopropyl and $R^{13}$ is methoxy.

35. A compound of claim 31 wherein $R^{14}$ is hydrogen.

36. A compound of claim 31 wherein $R^{14}$ is halogen.

37. A pharmaceutical composition comprising a therapeutically effective amount of a compound of claim 31 together with a pharmaceutically acceptable carrier or diluent.

38. The pharmaceutical composition of claim 37 administered in the form of an oral dosage or parenteral dosage unit.

39. The pharmaceutical composition of claim 38 wherein the compound is administered as a dose in the range from about 0.05 to 1000 mg per day.

40. A method of treating diabetes, comprising: administering to a subject in need thereof a therapeutically effective amount of a compound of claim 31.

41. A compound of claim 31 which is:

3-Isopropylamino-7-methoxy-4H-1,2,4-benzothiadiazine 1,1-dioxide, or a salt thereof with a pharmaceutically acceptable acid or base, or any optical isomer or mixture of optical isomers, or any tautomeric form.

42. A pharmaceutical composition comprising a therapeutically effective amount of a compound of claim 41 together with a pharmaceutically acceptable carrier or diluent.

43. The pharmaceutical composition of claim 42 administered in the form of an oral dosage or parenteral dosage unit.

44. The pharmaceutical composition of claim 43 wherein the compound is administered as a dose in the range from about 0.05 to 1000 mg per day.

45. A method of treating diabetes, comprising: administering to a subject in need thereof a therapeutically effective amount of a compound of claim 41.

46. A compound which is:

6-Fluro-3-isopropylamino-4H-1,2,4-benzothiadiazine 1,1-dioxide;

6-Chloro-7-fluro-3-isopropylamino-4H-1,2,4-benzothiadiazine 1,1-dioxide;

6,8-Dichloro-3-isopropylamino-4H-1,2,4-benzothiadiazine 1,1-dioxide;

8-Chloro-3-isopropylamino-4H-1,2,4-benzothiadiazine 1,1-dioxide; or

7-Fluro-3-isopropylamino-4H-1,2,4-benzothiadiazine 1,1-dioxide;

or a salt thereof with a pharmaceutically acceptable acid or base, or any optical isomer or mixture of optical isomers, or any tautomeric form.

47. A pharmaceutical composition comprising a therapeutically effective amount of a compound of claim 46 together with a pharmaceutically acceptable carrier or diluent.

48. The pharmaceutical composition of claim 47 administered in the form of an oral dosage or parenteral dosage unit.

49. The pharmaceutical composition of claim 48 wherein the compound is administered as a dose in the range from about 0.05 to 1000 mg per day.

50. A method of treating diabetes, comprising: administering to a subject in need thereof a therapeutically effective amount of a compound of claim 46.

51. A compound which is:

3-Ethylamino-6,7-difluoro-4H-1,2,4-benzothiadiazine 1,1-dioxide, or a salt thereof with a pharmaceutically acceptable acid or base, or any optical isomer or mixture of optical isomers, or any tautomeric form.

52. A pharmaceutical composition comprising a therapeutically effective amount of a compound of claim 51 together with a pharmaceutically acceptable carrier or diluent.

53. The pharmaceutical composition of claim 52 administered in the form of an oral dosage or parenteral dosage unit.

54. The pharmaceutical composition of claim 53 wherein the compound is administered as a dose in the range from about 0.05 to 1000 mg per day.

55. A method of treating diabetes, comprising: administering to a subject in need thereof a therapeutically effective amount of a compound of claim 51.

\* \* \* \* \*